United States Patent [19]

Takeuchi et al.

[11] Patent Number: 5,055,453

[45] Date of Patent: Oct. 8, 1991

[54] BENANOMICINS A AND ANTIBIOTIC COMPOSITIONS

[75] Inventors: Tomio Takeuchi; Takeshi Hara; Masa Hamada, all of Tokyo; Shinichi Kondo, Yokohama; Masaji Sezaki, Tokyo; Haruo Yamamoto, Chigasaki; Shuichi Gomi, Tokyo, all of Japan

[73] Assignee: Zaidan Hojin Biseibutsu Kagaku Kenkyu Kai, Tokyo, Japan

[21] Appl. No.: 264,888

[22] Filed: Oct. 31, 1988

[30] Foreign Application Priority Data

Nov. 2, 1987 [JP] Japan .................................. 62-277692
Dec. 25, 1987 [JP] Japan .................................. 62-327163

[51] Int. Cl.$^5$ ...................... A61K 31/70; C12P 19/56
[52] U.S. Cl. ...................................... 514/27; 536/6.4; 536/172; 536/18.1; 435/75; 435/252.1; 435/826
[58] Field of Search ................... 536/6.4, 18.1; 514/27

[56] References Cited

U.S. PATENT DOCUMENTS 4,870,165 9/1989 Oki et al. ............................ 536/6.4

Primary Examiner—Herbert J. Lilling
Attorney, Agent, or Firm—Larson and Taylor

[57] ABSTRACT

Two new antibiotics which are now nominated as benanomicin A and benanomicin B, respectively, are fermentatively produced by the cultivation of a new microorganism, designated as MH193-16F4 strain, of Actinomycetes. Benanomicins A and B each show antifungal activity and are useful as a therapeutic antifungal agent. A new compound, dexylosylbenanomicin B is now produced by chemical conversion of benanomicin B, and this semi-synthetic antibiotic also shows antifungal activity and is useful as a therapeutic antifungal agent.

3 Claims, 12 Drawing Sheets

BENANOMICINS A AND ANTIBIOTIC COMPOSITIONS

SUMMARY OF THE INVENTION

This invention relates to new antifungal antibiotics which are respectively nominated as benanomicin A, benanomicin B and dexylosylbenanomicin B, and which each are useful as a therapeutic antifungal agent and may be present in the form of their salts or their esters. This invention also relates to a process for the fermentative production of benanomicins A and B, as well as a process for the production of dexylosylbenanomicin B from benanomicin B. This invention further relates to a pharmaceutical composition comprising benanomicin A, benanomicin B or dexylosylbenanomicin B as active ingredient.

BACKGROUND OF THE INVENTION

Many antibiotics are already known, but new antibiotic substances are still wanted to be provided in the pharmaceutical field and also in the agricultural field. We, the present inventors, have made extensive researches to discover and provide new antibiotic substances which can exhibit useful antibacterial activity and/or antifungal activity. As a result, we have now found that when a microbial strain of the genus Actinomycetes, which was isolated from a soil sample collected out of the ground in our laboratory in Tokyo, Japan and which was given a laboratory designation of MH193-16F4 strain, is cultivated in a culture medium under aerobic conditions, there are produced some antibiotics which exhibit antifungal activities. We have succeeded in isolating and purifying two antifungal antibiotics from the culture of the MH193-16F4 strain, and we have nominated these isolated two antibiocits as benanomicin A and benanomicin B, respectively. We have studied the physicochemical and biological properties of benanomicins A and B to confirm that benanomicins A and B are new substances distinguishable from any of the known antibiotics. Through our further study, we have now succeeded in deciding the chemical structures of benanomicins A and B. Furthermore, we have now succeeded in synthetizing a new compound, namely dexylosylbenanomicin B by a chemical conversion of benanomicin B and have found that dexylosylbenanomicin B also can exhibit a useful antifungal activity.

We have further found that the new antibiotics, benanomicins A and B according to this invention are more or less similar in their physicochemical and biological properties as well as in their chemical structures to known three antibiotics, namely KS-619-1 substance {Matsuda et al: the "Journal of Antibiotics" 40, 1104–1114(1987)}; and G-2N substance and G-2A substance {Gerber et al: the "Canad. J. Chem." 62, 2818–2821 (1984)}, but that benanomicins A and B can clearly be differentiated from the above-mentioned known three antibiotics in view of their physicochemical and biological properties and also their chemical structures.

Hithertobefore, a variety of antibotics which are produced by microorganisms are already known. Among the known antibiotics, however, such antibiotics which can exhibit a useful antifungal activity but a low toxicity to mammals are only few. Accordingly, there is always a demand for discovery and exploitation of a new antifungal antibiotic which is useful in the therapeutic treatment of various fungal infections in an animal, including human. We have now found that benanomicins A and B as well as dexylosylbenanomicin B are of a low toxicity to an animal and that they can be represented by a general formula (I) shown hereinafter.

Therefore, an object of this invention is to provide new antibiotics which can exhibit a usefully high antifungal activity with a low toxicity to mammals, and more particularly benanomicin A, benanomicin B and dexylosylbenanomicin B as well as their pharmaceutically acceptable salts and esters. Another object of this invention is to provide processes for the production of these new antibiotics. Further objects of this invention will be apparent from the following descriptions.

DETAILED DESCRIPTION OF THE INVENTION

In a first aspect of this invention, therefore, there are provided a compound having the general formula (I)

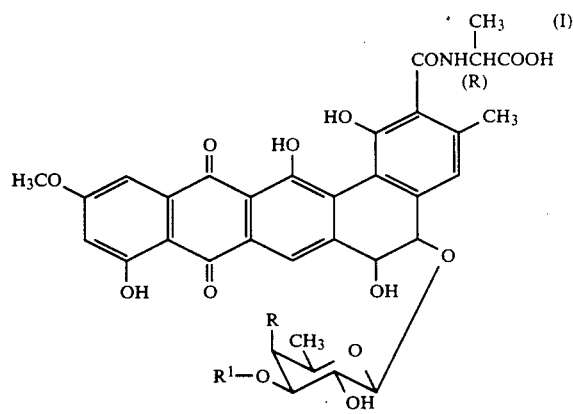

wherein R is a hydroxyl group or an amino group and $R^1$ is a hydrogen atom or a xylosyl group, provided that when R is the hydroxyl group, $R^1$ is not the hydrogen atom, and a salt or an ester of the compound of the formula (I).

Such a compound of the general formula (I), where R is a hydroxyl group and $R^1$ is a xylosyl group of the formula

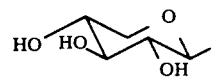

is benanomicin A of the formula (Ia)

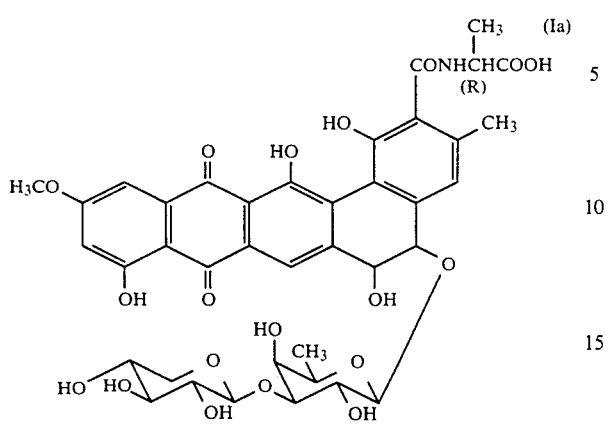

(Ia)

Such a compound of the general formula (I), where R is an amino group and R¹ is the xylosyl group, is benanomicin B of the formula (Ib)

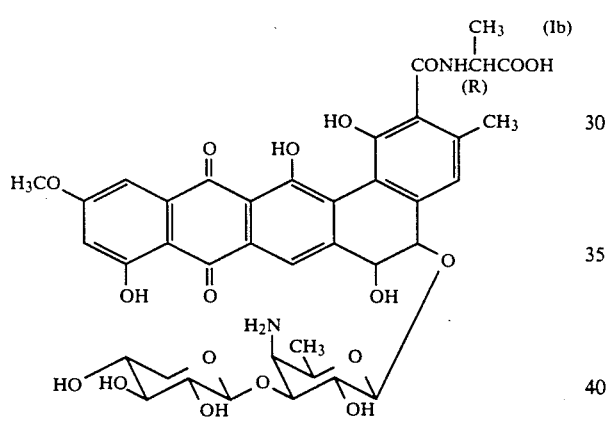

(Ib)

Such compound of the general formula (I), where R is an amino group and R¹ is the hydrogen atom, is dexylosylbenanomicin B of the formula (Ic)

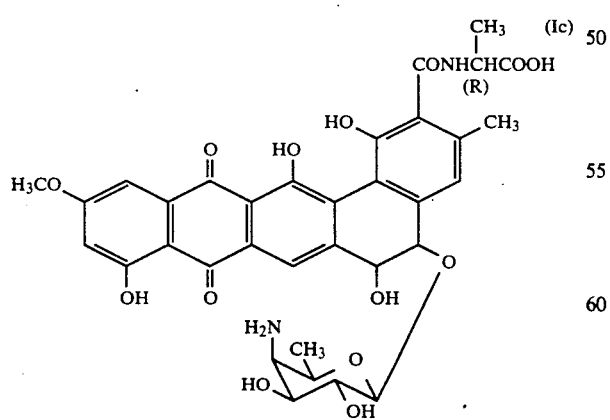

(Ic)

Benanomycin A and benanomycin B may collectively be represented by a general formula (I')

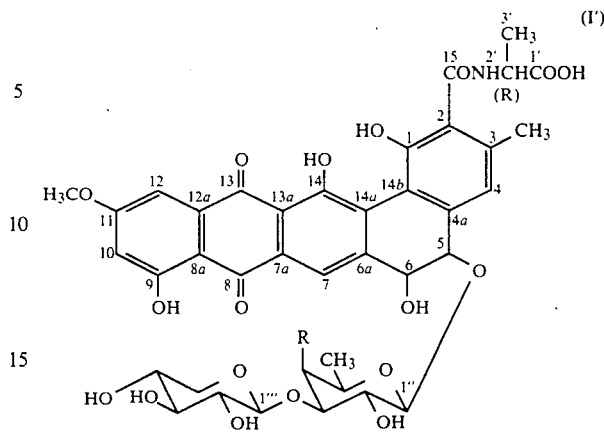

(I')

wherein R is a hydroxyl group for benanomicin A and R is an amino group for benanomicin B.

Before the chemical structure of benanomicin A has been elucidated as above, benanomicin A has firstly be obtained and identified as such an antibiotic substance having the following characteristics that it is an acidic substance in the form of a reddish brown powder, shows an empirical formula $C_{39}H_{41}NO_{19}$, a mass spectrum (FD-MS) of m/z 827 (M+), a melting point higher than 220° C., an ultraviolet and visible-ray absorption spectrum (in methanol) as shown in FIG. 1 of the accompanying drawings, an infrared absorption spectrum (pelleted in potassium bromide) as shown in FIG. 2 of the accompanying drawings, a $^1$H-NMR spectrum (400 MHz, DMSO-$d_6$, 40° C.) as shown in FIG. 3 of the accompanying drawings and a $^{13}$C-NMR spectrum (100 MHz, DMSO-$d_6$) as shown in FIG. 4 of the accompanying drawings, and is only sparingly soluble in methanol, chloroform, ethyl acetate and acetone and is soluble in dimethylsulfoxide, dimethylformamide and alkaline water but is insoluble in water.

Before the chemical formula of benanomicin B has been elucidated as above, benanomicin B has at first been obtained and identified as such an antibiotic substance having the following characteristics that the hydrochloride of benanomicin B is an amphoteric substance in the form of a reddish brown powder, shows an empirical formula $C_{39}H_{42}N_2O_{18}\cdot HCl$, a mass spectrum (SI-MS) of m/z 827 (MH+) a melting point higher than 220° C., a specific rotation $[\alpha]_D^{22}$ +360° (c 0.05, $H_2O$), an ultraviolet and visible-ray absorption spectrum (in methanol) as shown in FIG. 5 of the accompanying drawings, an infrared absorption spectrum (pelleted in potassium bromide) as shown in FIG. 6 of the accompanying drawings, a $^1$H-NMR spectrum (400 MHz, DMSO-$d_6$, 40° C.) as shown in FIG. 7 of the accompanying drawings and a $^{13}$C-NMR spectrum (100 MHz, DMSO-$d_6$) as shown in FIG. 8 of the accompanying drawings, and is only sparingly soluble in chloroform, ethyl acetate and acetone and is soluble in methanol, dimethylsulfoxide, dimethylformamide and water.

1. The above-mentioned and further physicochemical properties of benanomicin A are listed below in more detail:

(1) Color and appearance: Reddish brown powder.
(2) Empirical formula: $C_{39}H_{41}NO_{19}$.
(3) Mass spectrum (FD-MS): m/z 827 (M+).
(4) Melting point: >220° C.

(5) Specific rotation: $[\alpha]_D^{22}$ Unmeasurable (c 0.05, DMSO)

(6) Ultraviolet and visible-ray absorption spectrum. λmax, nm $(E_1\%_{cm})$: {In methanol}: 206(718), 230sh(600), 288(482), 302sh(390), 400sh(120), 476(197). {In 0.1 N HCl-methanol}: 207(649), 233(629), 298(561), 395sh(140), 457(223). {In 0.1 N NaOH-methanol}: 214(1270), 249(637), 320(289), 498(287).

(7) Infrared absorption spectrum (KBr, cm$^{-1}$) 3350, 2970, 2890, 1720, 1620, 1600, 1485, 1440, 1425, 1390, 1375, 1330, 1295, 1255, 1235, 1205, 1160, 1130, 1070, 1040, 1000, 970, 900, 870, 830, 800, 750.

(8) $^1$H-NMR spectrum (400 MHz, in DMSO-d$_6$, at 40° C.): δ(ppm) : 1.14(3H, d), 1.35(3H, d), 2.34 (3H, s), 3.09(1H, dd), 3.13(1H, dd), 3.17(1H, dd), 3.32(1H, ddd), 3.56(1H,dd), 3.62(2H, m), 3.72 (1H, dd), 3.74(1H, br), 3.92(3H, s), 4.43(1H, d), 4.43(1H, dq), 4.53(1H,d), 4.57(1H, d), 4.65 (1H, d), 4.90(2H, br), 5.61(1H, br), 6.05(1H, br), 6.86(1H, d) 7.21(1H, s), 7.24(1H, d), 8.05 (1H, s), 8.45(1H, d), 12.47 (1H, br), 12.77 (1H, s) 13.69 (1H, br).

(9) $^{13}$C-NMR spectrum (100 MHz, in DMSO-d$_6$, at 40° C.): δ(ppm) : 187.3 s, 184.9 s, 173.9 s, 166.9 s, 165.9. s, 164.7 s, 156.8 s, 151.1s, 147.7 s, 138.1 s, 137.4 s, 134.2 s, 131.3 s, 127.5 s, 125.6 s, 118.6 d 115.5 s, 115.4 d, 113.7 s, 110.0 s, 107.5 d, 106.8 d, 105.2 d, 104.4 d, 83.0 d, 81.7 d, 76.0 d, 73.6 d, 71.9 d, 70.3 d, 70.1 d, 70.1 d, 69.4 d, 65.6 t, 56.3 q, 47.6 d, 19.1 q, 16.9 q, 16.3 q. (The signals at 72.9, 81.7, 115.4 and 118.6 ppm are broad.)

(10) Solubility: Only sparingly soluble in methanol, chloroform, ethyl acetate and acetone, soluble in dimethylsulfoxide, dimethylformamide and alkaline water, but insoluble in water.

(11) Distinction between the basic, acidic and neutral natures of substance: Acidic substance 2. The above-mentioned and further physicochemical properties of benanomicin B hydrochloride are listed below in more detail:

(1) Color and appearance: Reddish brown powder
(2) Empirical formula: $C_{39}H_{42}N_2O_{18}.HCl$
(3) Mass spectrum (SI-MS) m/z 827 (MH+)
(4) Melting point: >220° C.
(5) Specific rotation: $[\alpha]_D^{22}$ +360° (c 0.05, H$_2$O).

(6) Ultraviolet and visible-ray absorption spectrum, λmax, nm $(E_1\%_{cm})$: {In methanol}: 205(587), 233(526), 296(426), 390sh(100), 458(169). {In 0.1 N HCl-methanol}: 207(514), 235(530), 295(442), 400sh(114), 457(173). {In 0.1 N NaOH-methanol}: 214(1219), 247(518), 317(238), 496(215).

(7) Infrared absorption spectrum (KBr, cm$^{-1}$): 3350, 2980, 2900, 1720, 1610, 1485, 1350, 1430, 1395, 1380, 1330, 1300, 1260, 1240, 1210, 1160, 1080, 1045, 970, 955, 900, 885, 840, 820.

(8) $^1$H-NMR spectrum (400 MHz, in DMSO-d$_6$, at 40° C.): 1.20(3H, d), 1.36(3H, d), 2.35 (3H, s), 3.09(1H, dd), 3.17(1H, m), 3.19 (1H, m), 3.34(1H, ddd), 3.44 (1H, br), 3.65(1H, br), 3.75 (1H, dd), 3.90(1H, br q), 3.94 (3H, s), 3.97(1H, dd), 4.44(1H, dq) 4.57(1H, d), 4.57(1H, br d) 4.62 (1H, br d), 4.75(1H, d), 6.90(1H, d), 7.27(1H, d), 7.27(1H, br s), 7.99 (3H, br), 8.06(1H, br s), 8.45(1H, d), 8.45(1H, br), 12.79(1H, s), 13.81(1H, br), 4.1-6.3(5H, br).

(9) $^{13}$C-NMR spectrum (100 MHz, in DMSO-d$_6$, at 40° C.): δ(ppm):187.4 s, 184.9 s, 173.9 s, 166.9 s, 165.9 s, 164.7 s, 156.8 s, 151.0 s, 148.0 s, 137.8 s, 137.3 s, 134.2 s, 131.2 s, 127.5 s, 125.7 s, 118.9 d, 115.9 d, 115.5 s, 113.7 s, 110.0 s, 107.6 d, 106.8 d, 104.4 d, 104.1 d, 81.0 d, 77.4 d, 75.9 d, 73.3 d, 71.5 d, 69.8 d, 69.4 d, 67.0 d, 65.7 t, 56.3 q, 54.2 d, 47.6 d, 19.1 q, 16.9 q, 16.3 q. (The signals at 71.5, 81.0, 113.7, 115.9, 118.9 and 125.7 ppm are broad.).

(10) Solubility: Only sparingly soluble in chloroform, ethyl acetate and acetone, and soluble in methanol, dimethylsulfoxide, dimethylformamide and water.

(11) Distinction between the basic, acidic and neutral natures of substance: Amphoteric substance 3. Physicochemical properties of dexylosylbenanomicin B hydrochloride are listed below.

(1) Color and appearance: Reddish brown powder
(2) Empirical formula: $C_{34}H_{34}N_2O_{14}.HCl$.
(3) Mass spectrum (SD-MS): m/z 696 (M+2)+.
(4) Melting point: >180° C. (decomposed).
(5) Specific rotation: $[\alpha]_D^{24}$+396°. (c 0.05, 0.05 N HCl).

(6) Ultraviolet and visible-ray absorption spectrum, λmax, nm $(E_1\%_{cm})$: {In methanol}: 204 (569), 234 (517) 290 (431), 300sh (395), 400sh (110), 463 (170). {In 0.1 N HCl-methanol}: 209 (522), 234 (557), 296 (487), 400sh (130), 459 (196). {In 0.1 N NaOH-methanol}: 213 (1205), 249 (575), 258sh (520), 319 (259), 496 (251).

(7) Infrared absorption spectrum (KBr, cm$^{-1}$): 3400, 2980, 2910, 1730, 1610, 1515, 1490, 1450, 1435, 1395, 1380, 1340, 1300, 1260, 1240, 1210, 1170, 1130, 1090, 1030, 1005, 980, 880, 835.

(8) $^1$H-NMR spectrum (400 MHz, in DMSO-d$_6$, at 40° C.): δ(ppm): 1.18 (3H, d), 1.34 (3H, d), 2.33 (3H, s), 3.26 (1H, br s), 3.47 (1H, br), 3.74 (1H, br dd), 3.86 (1H, br q), 3.96 (3H, s), 4.43 (1H, dq), 4.53 (1H, br d), 4.60 (1H, br d), 4.68 (1H, d), 6.94 (1H, d), 7.25 (1H, br s), 7.31 (1H, d), 7.87 (3H, br), 8.08 (1H, s), 8.45 (1H, d), 8.60 (1H, br), 12.82 (1H, s), 13.81 (1H, br)

(9) $^{13}$C-NMR spectrum (100 MHz, in DMSO-d$_6$, at 40° C.): δ(ppm): 187.4 s, 184.9 s, 173.8 s, 166.8 s, 165.9 s, 164.7 s, 156.8 s, 150.9 s, 147.9 s, 137.9 s, 137.2 s, 134.2 s, 131.2 s, 127.4 s, 125.7 s, 118.8 d, 115.5 s, 115.5 s, 113.6 s, 110.0 s, 107.5 d, 106.8 d, 104.6 d, 81.1 d, 71.5 d, 70.5 d, 69.8 d,.67.1 d, 56.4 q, 54.6 d, 47.6 d, 19.1 q, 16.8 q, 16.3 q. (The signals at 115.5 and 118.8 ppm are broad.).

(10) Solubility: Only sparingly soluble in chloroform, ethyl acetate and acetone, and soluble in water, methanol, dimethylsulfoxide, and dimethylformamide.

(11) Distinction between the basic, acidic and neutral natures of substance: Amphoteric substance.

With reference to the accompanying drawings.

Figure 1:
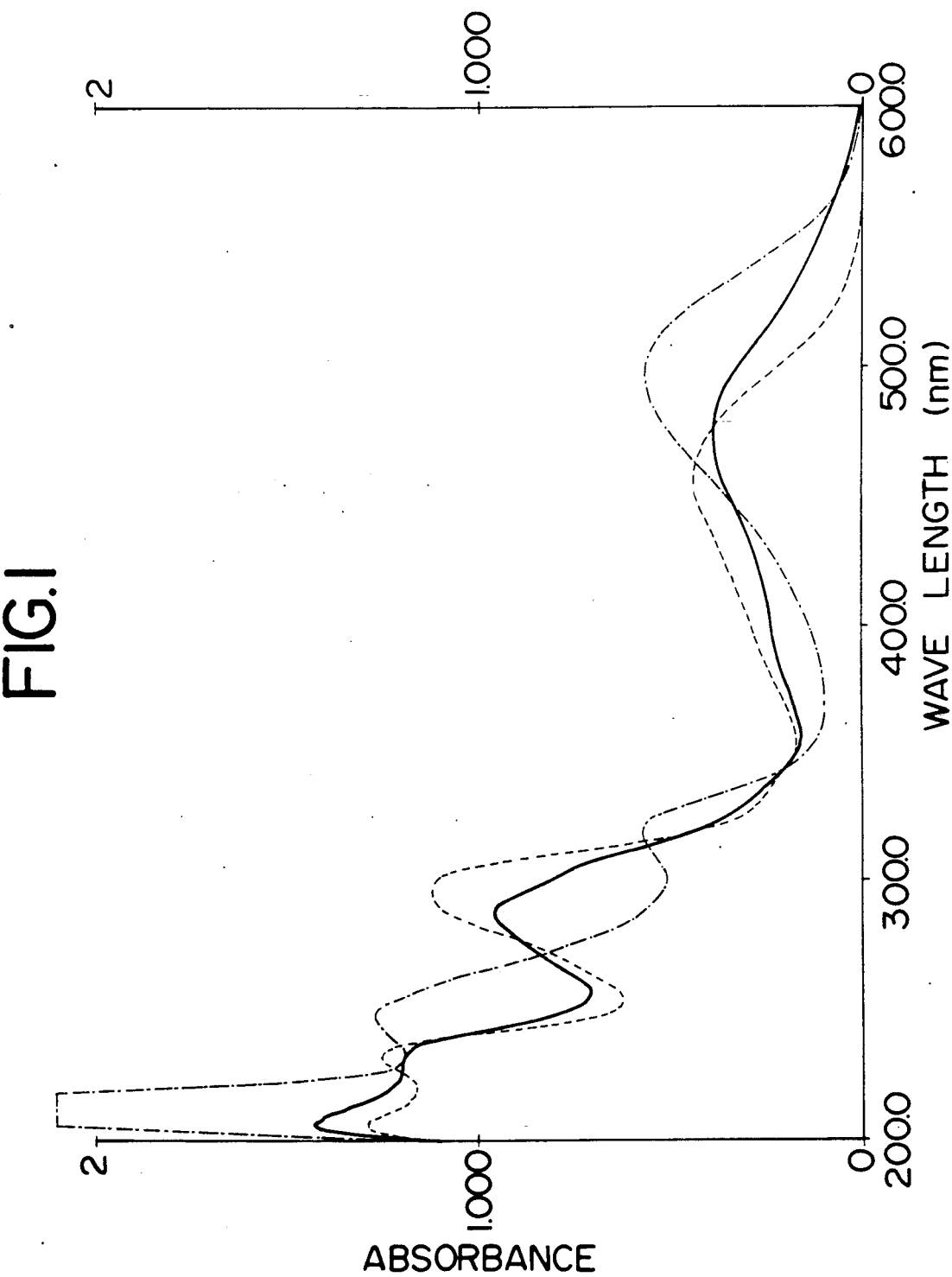
FIG. 1 is a UV and visible-ray absorption spectrum of benanomicin A in methanol (20 μg/ml)
Figure 2:
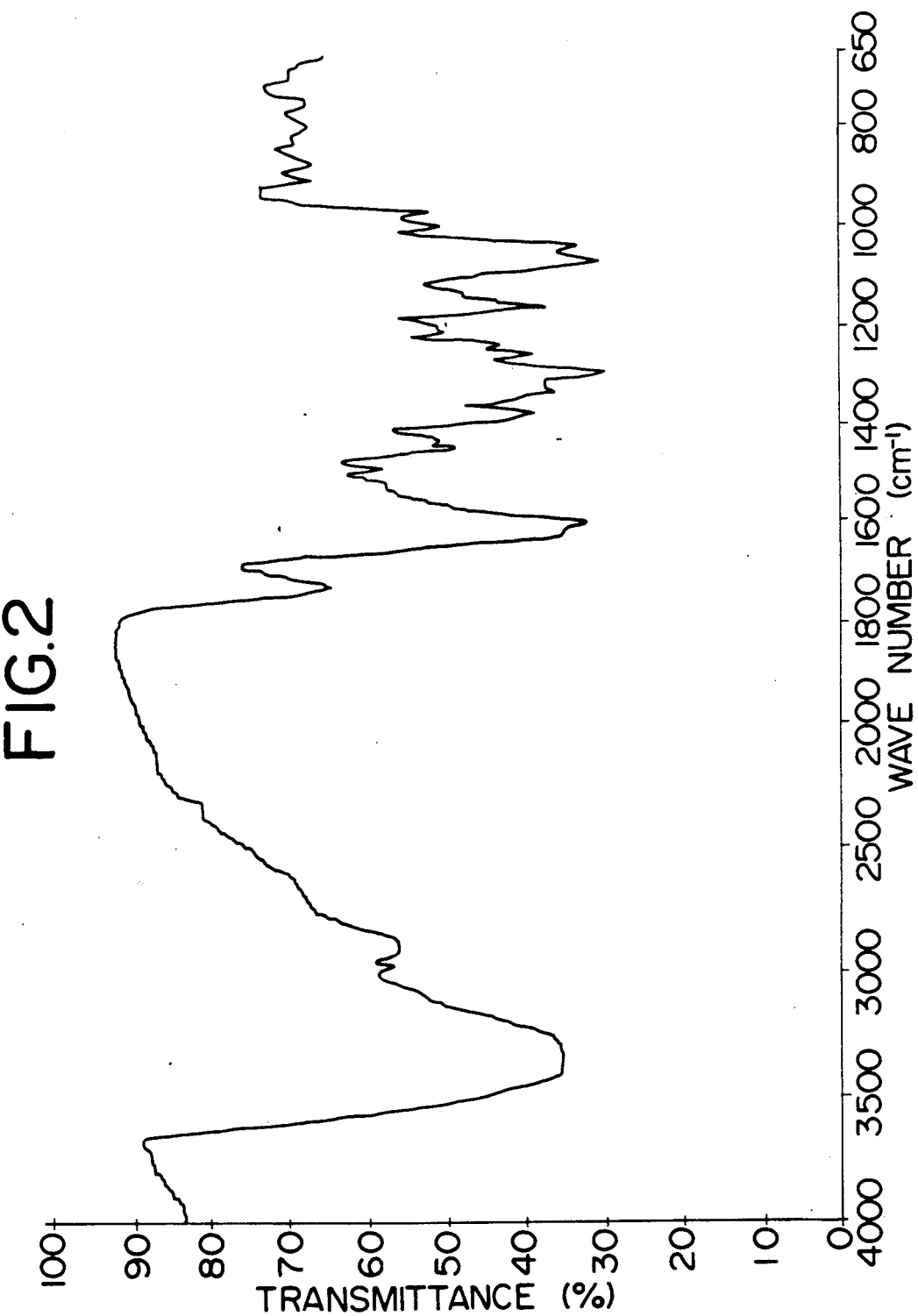
FIG. 2 is an IR absorption spectrum of benanomicin A as pelleted in potassium bromide.
Figure 3:
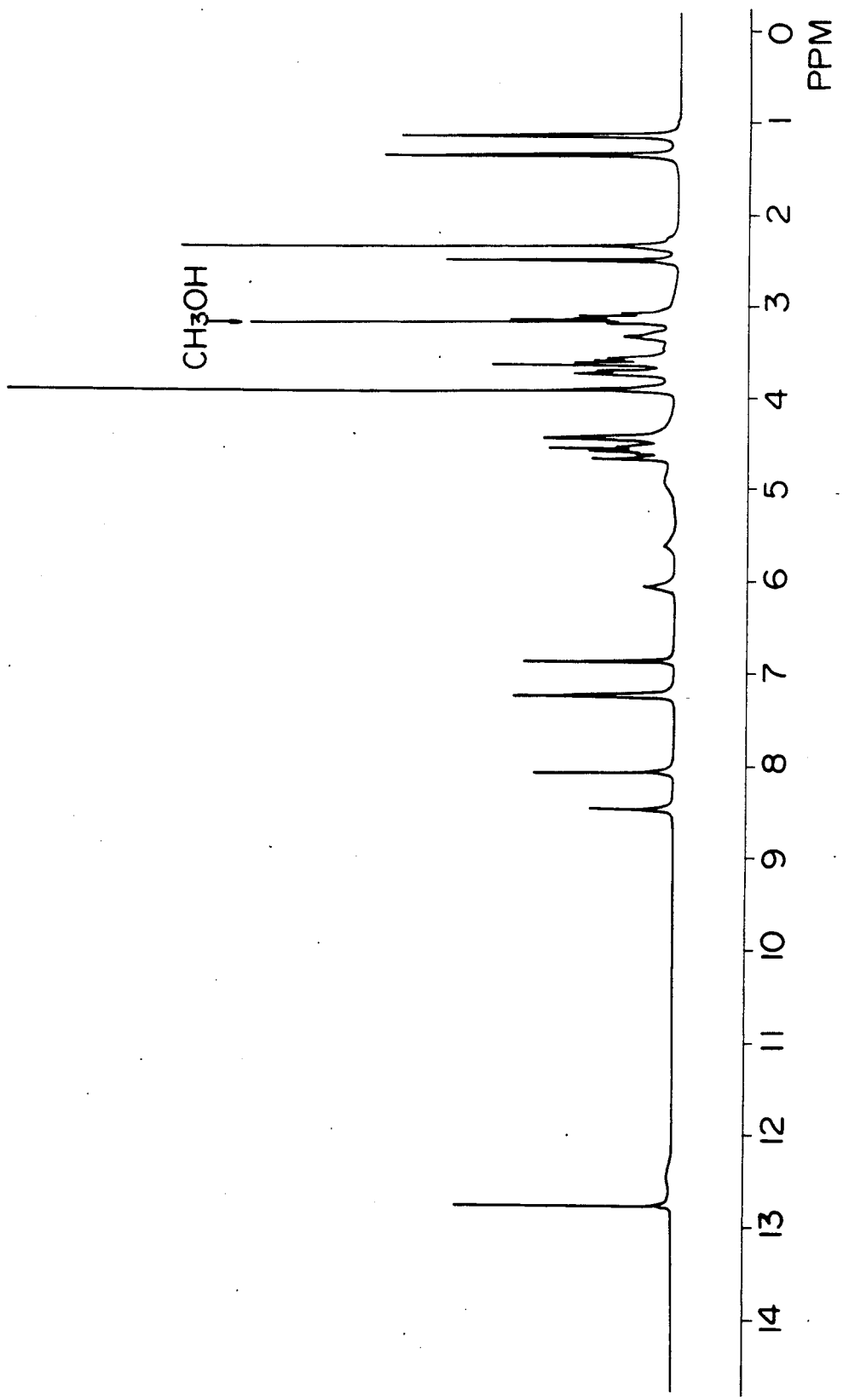
FIG. 3 is a $^1$H-NMR absorption spectrum of benanomicin A as measured at 400 MHz in deutero-dimethylsulfoxide (DMSO-d$_6$)
Figure 4:
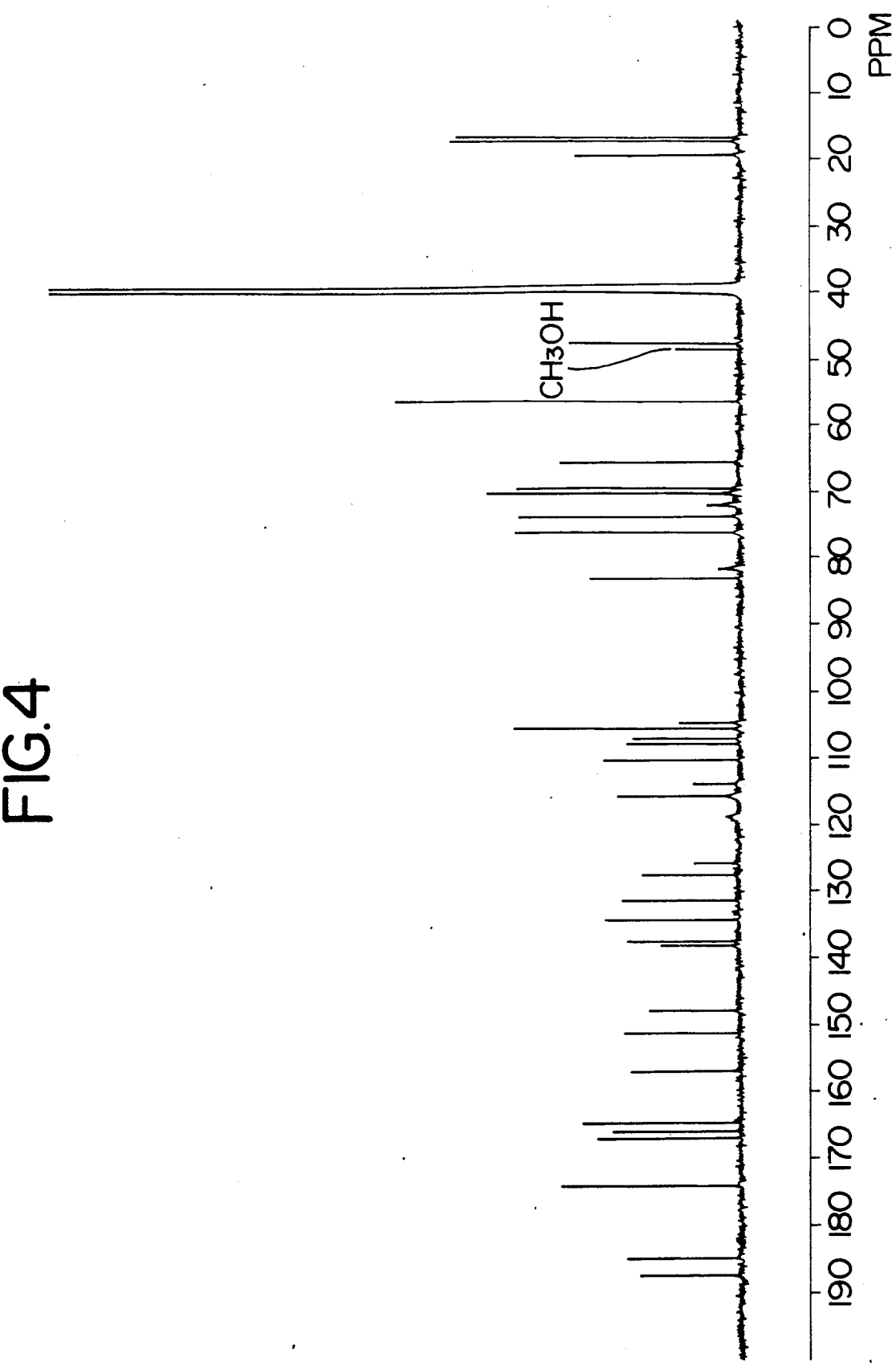
FIG. 4 is a $^{13}$C-NMR absorption spectrum of benanomicin A as measured at 100 MHz in deutero-dimethylsulfoxide (DMSO-d$_6$)
Figure 5:
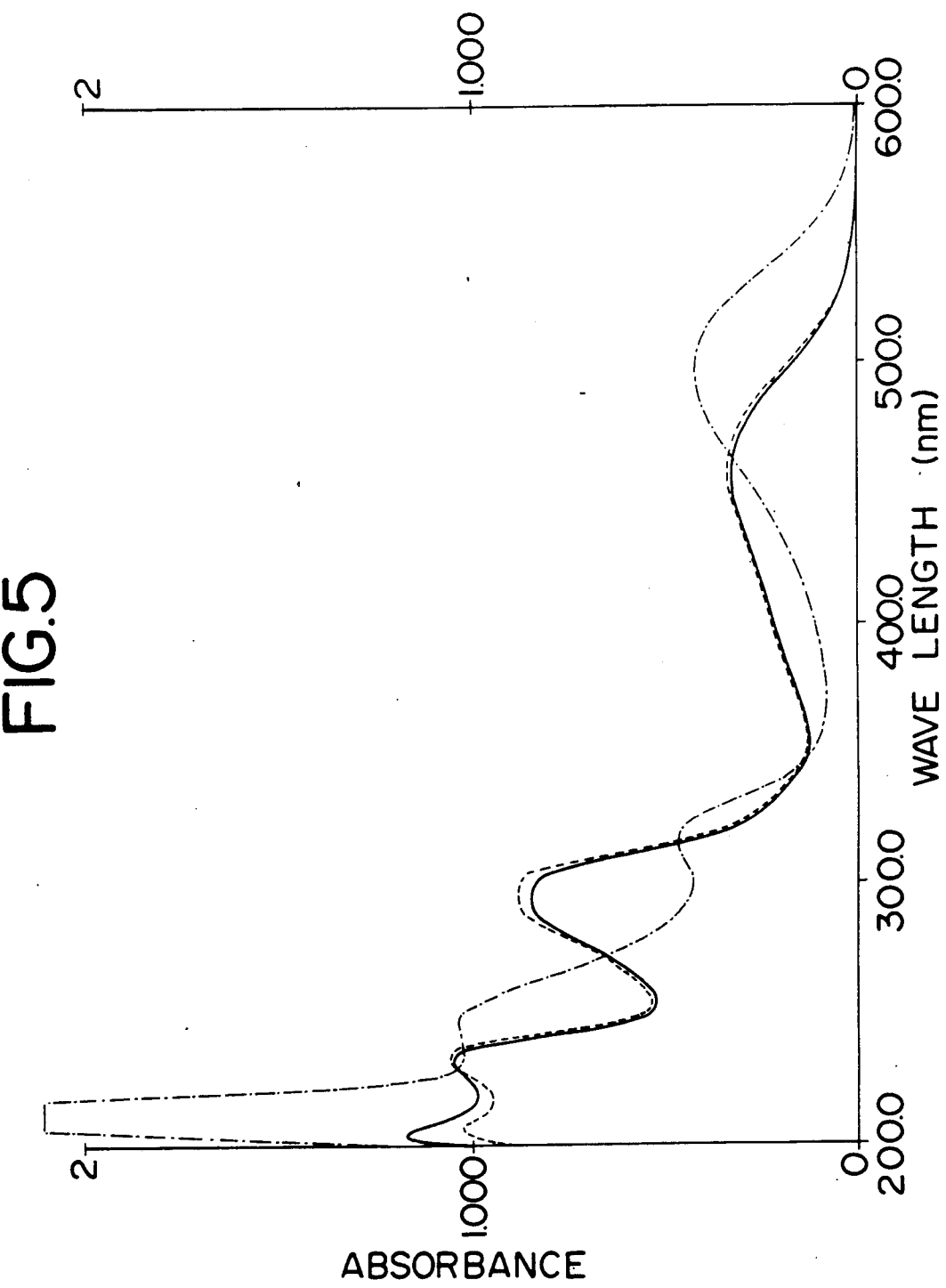
FIG. 5 is a UV and visible-ray absorption spectrum of benanomicin B hydrochloride in methanol (20 μg/ml)
Figure 6:
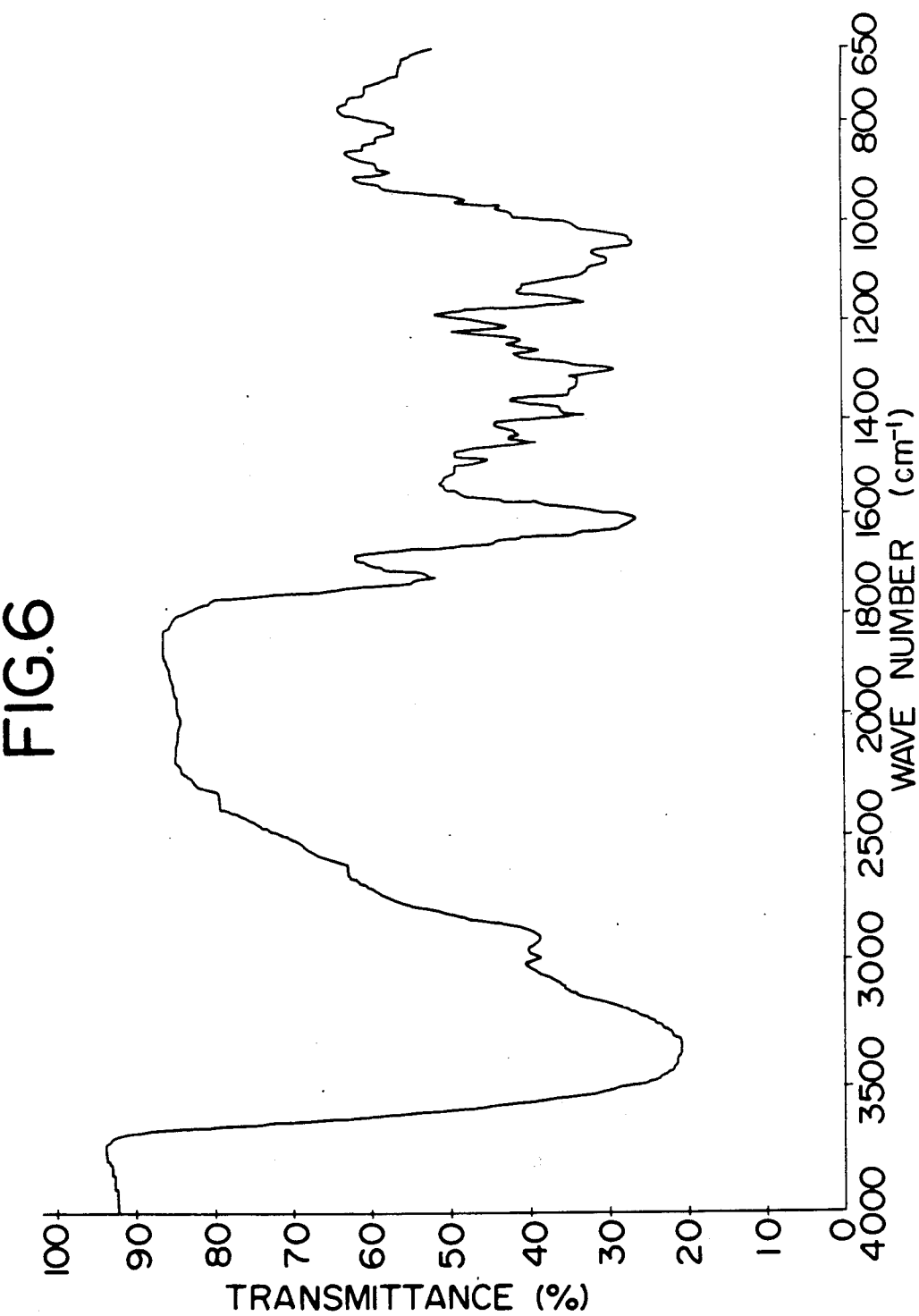
FIG. 6 is an IR absorption spectrum of benanomicin B hydrochloride as pelleted in potassium bromide.
Figure 7:
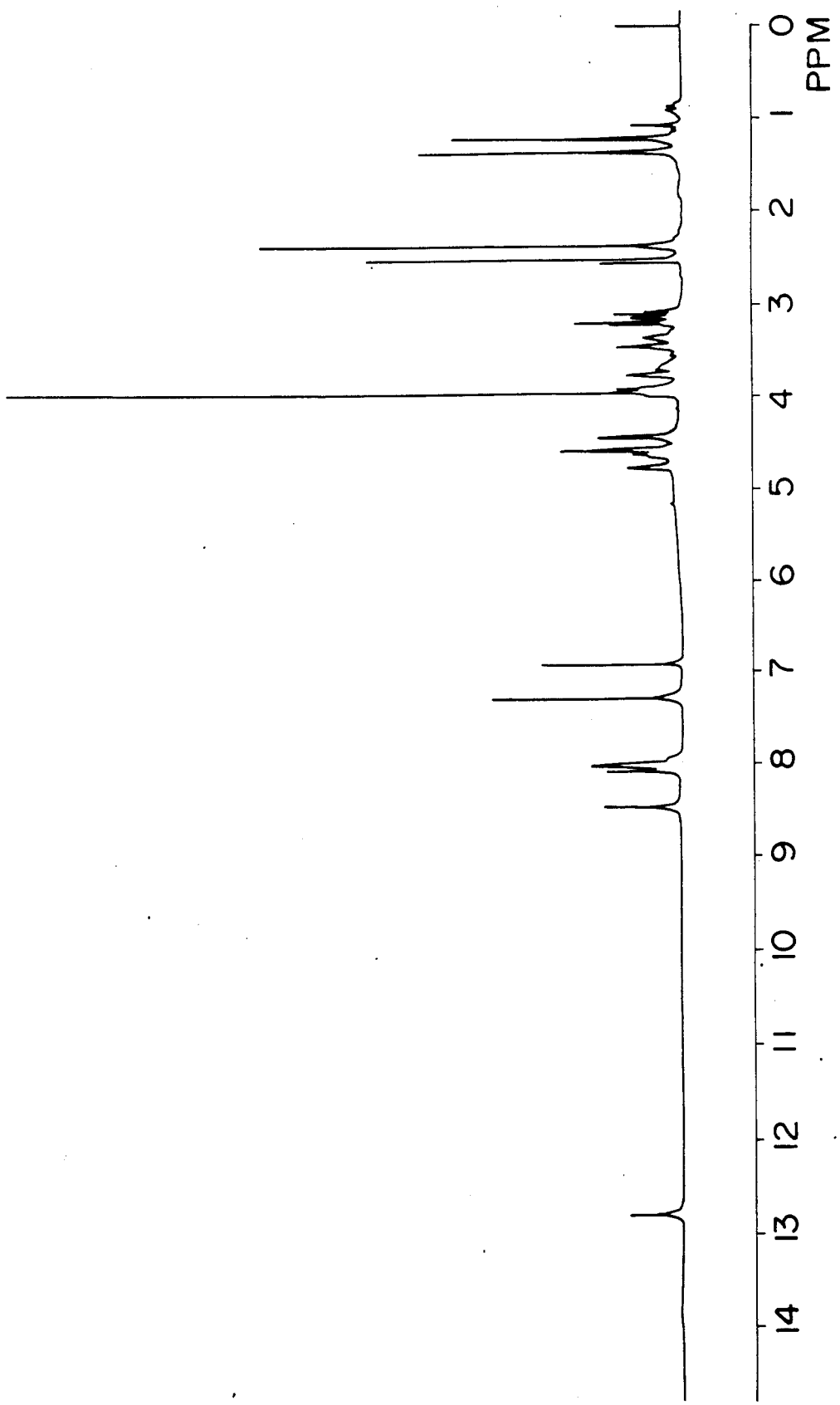
FIG. 7 is a $^1$H-NMR absorption spectrum of benanomicin B hydrochloride as measured at 400 MHz in deutero-dimethylsulfoxide.
Figure 8:
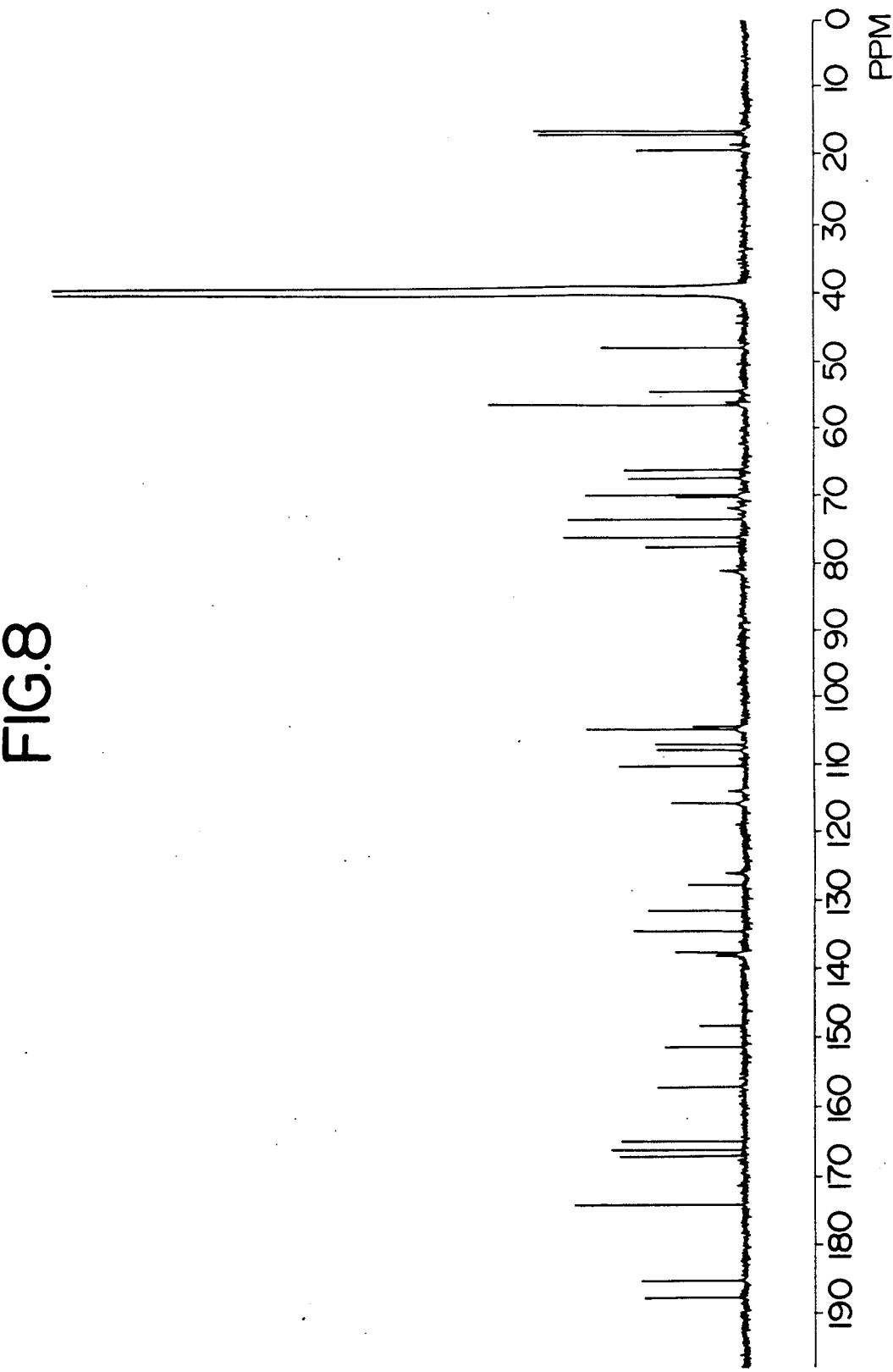
FIG. 8 is a $^{13}$C-NMR absorption spectrum of benanomicin B hydrochloride as measured at 100 MHz in deutero-dimethylsulfoxide.
Figure 9:
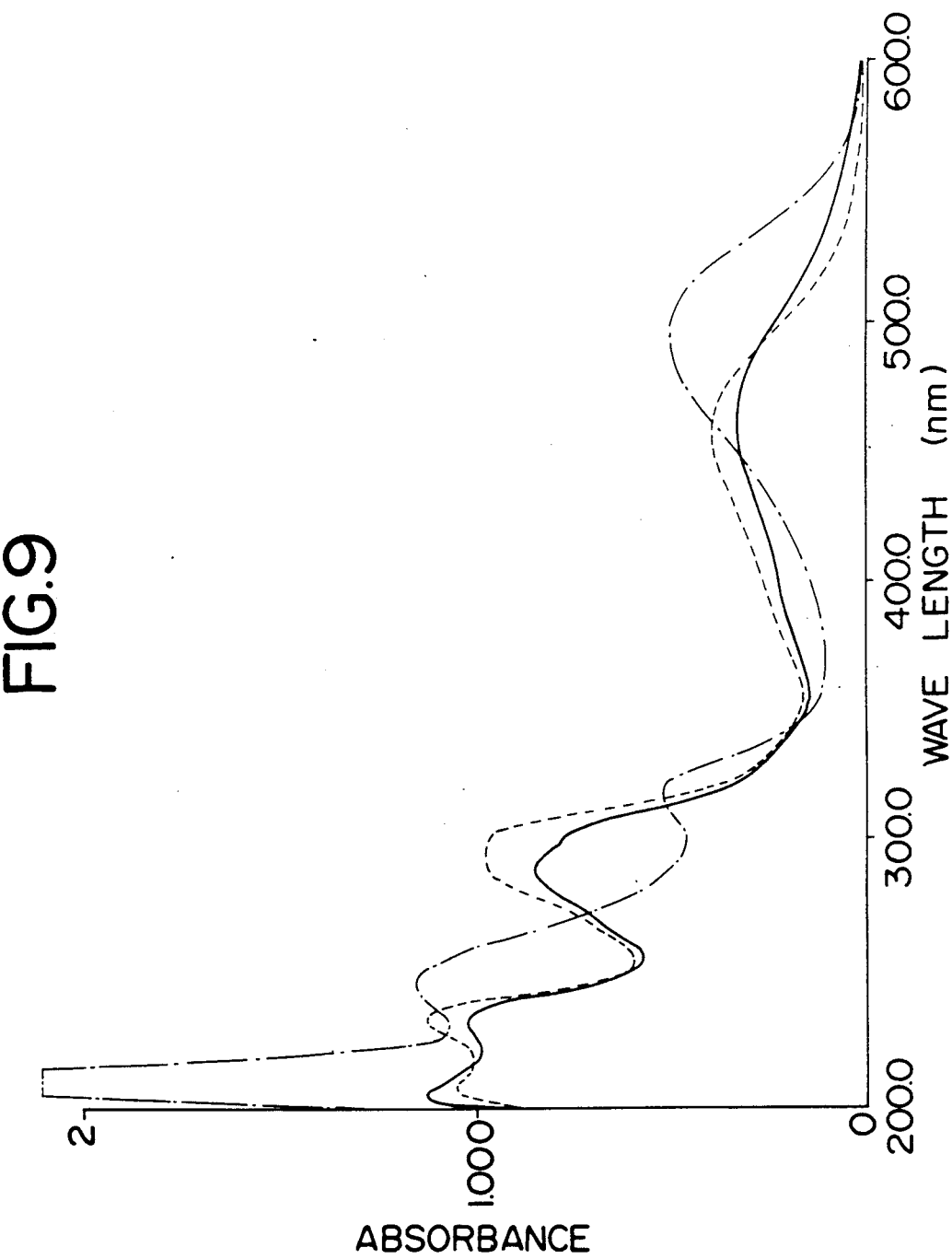
FIG. 9 is a UV and visible-ray absorption spectra of dexylosylbenanomicin B hydrochloride as measured in methanol (20 μg/ml) (of which spectrum is indicated by a solid curve), in 0.1 N hydrochloric acid-ethanol (20 μg/ml) (of which spectrum is indicated by a broken curve) and in 0.1 N sodium hydroxide-ethanol (20 μg/ml) (of which spectrum is shown by a dotted curve), respectively.
Figure 10:
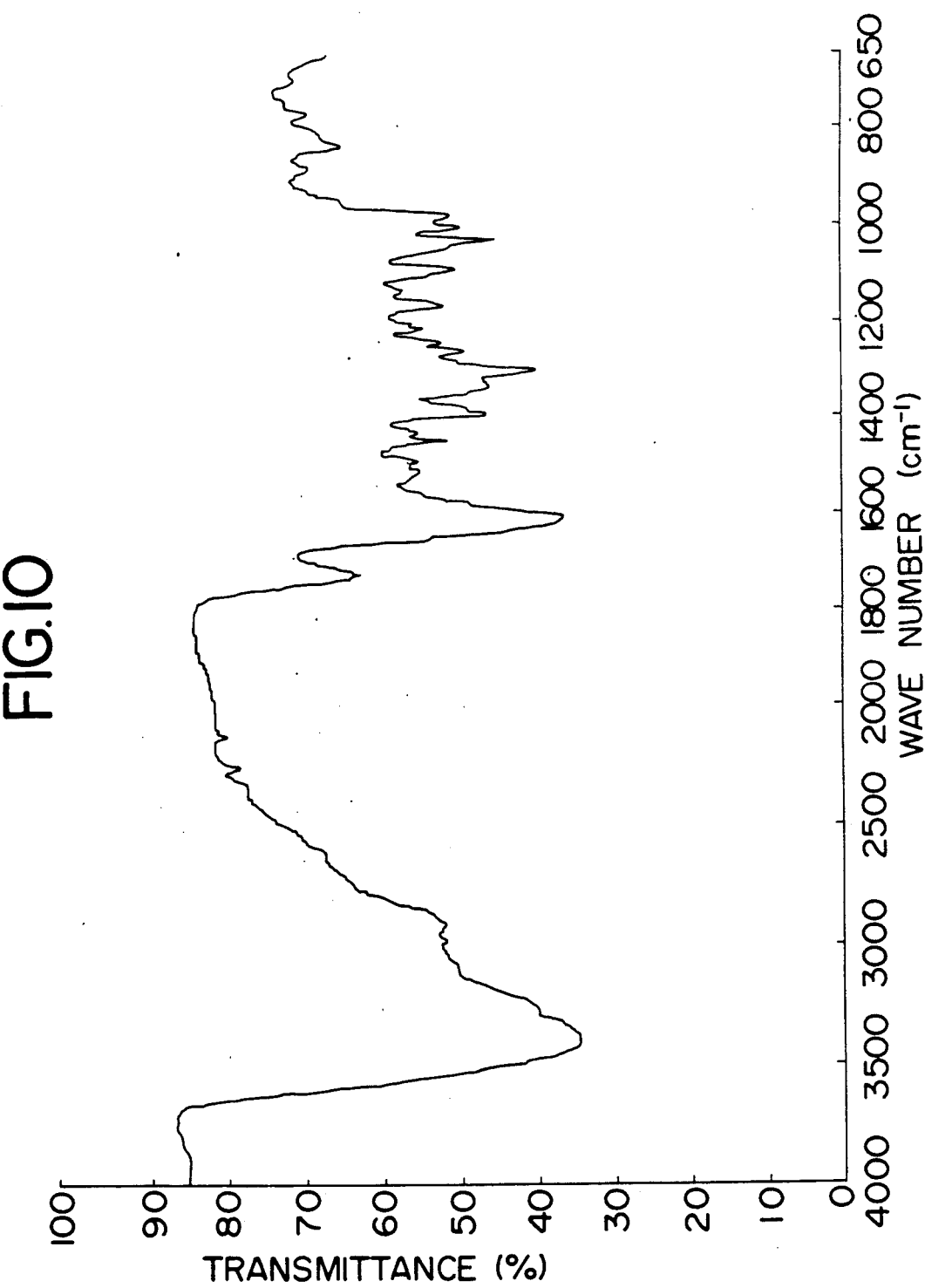
FIG. 10 is an IR absorption spectrum of dexylosylbenanomicin B hydrochloride as pelleted in potassium bromide.
Figure 11:
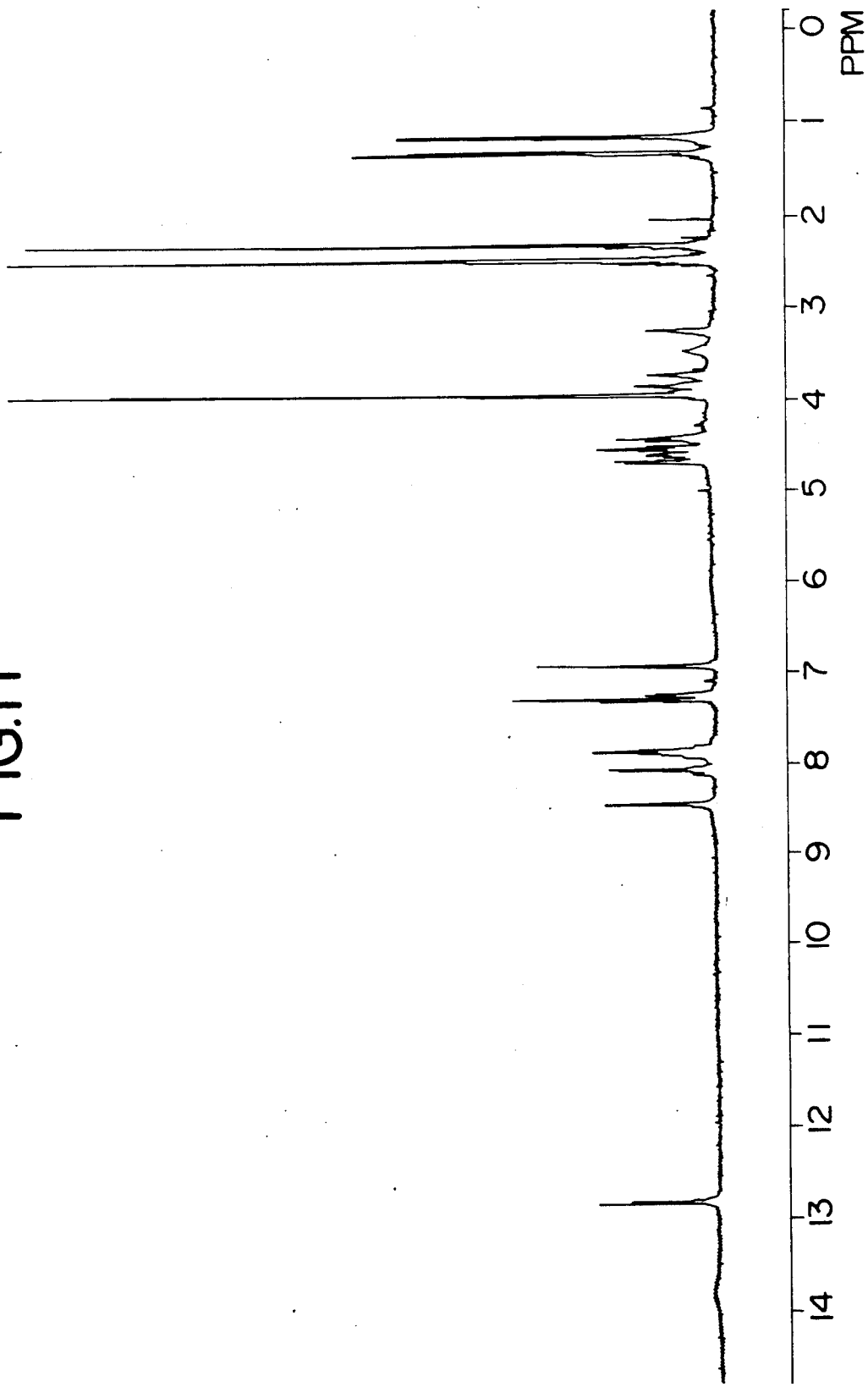
FIG. 11 is a $^1$H-NMR absorption spectrum of dexylosylbenanomicin B hydrochloride as measured at 400 MHz in deutero-dimethylsulfoxide.
Figure 12:
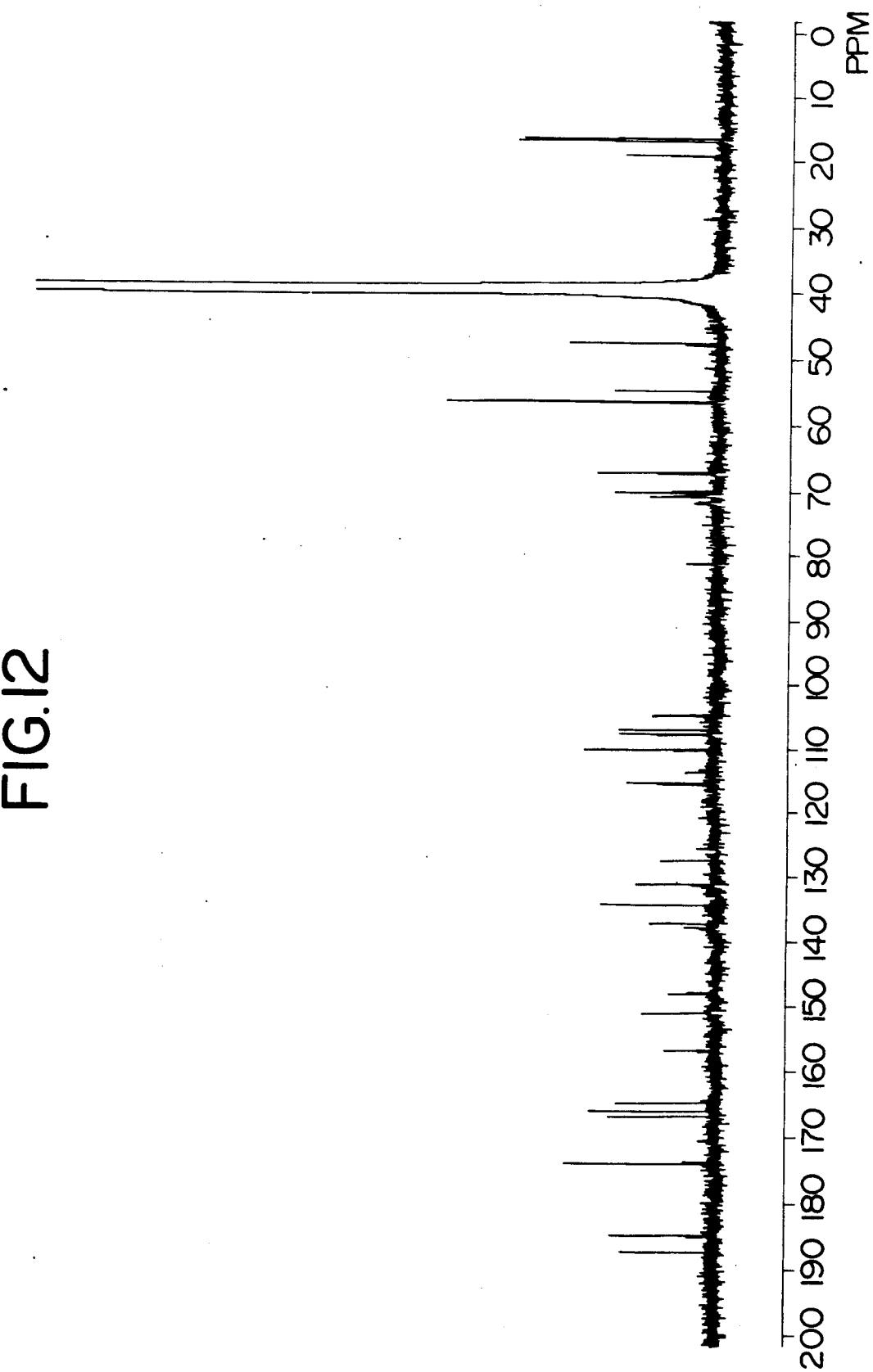
FIG. 12 is a $^{13}$C-NMR absorption spectrum of dexylosylbenanomicin B hydrochloride as measured at 100 MHz in deutero-dimethylsulfoxide.

Salts of the compound of the general formula (I), namely benanomicins A and B and dexylosylbenanomicin B, include a pharmaceutically acceptable salts (the carboxylate) with a pharmaceutically acceptable metal, particularly a pharmaceutically acceptable alkali metal such as sodium and potassium and a pharmaceutically acceptable alkaline earth metal such as calcium and magnesium, and ammonium group, as well as a pharmaceutically acceptable base-addition salt (at the carboxyl group of the compound) with a pharmaceutically acceptable organic base, particularly an amine, such as a lower ($C_1$-$C_6$) alkyl amine, especially triethylamine, ethanolamine and dicyclohexylamine, and also, in the case of benanomicin B and dexylosylbenanomicin B, a pharmaceutically acceptable acid-addition salt (at the amino group) with a pharmaceutically acceptable inorganic acid such as hydrochloric acid, sulfuric acid, phosphoric acid and nitric acid or a pharmaceutically acceptable organic acid such as acetic acid, propionic acid, maleic acid and an alkylsulfonic acid. Esters of the compound of the general formula (I) include a pharmaceutically acceptable ester (the carboxylate) with a pharmaceutically acceptable ester-forming radical such as a lower ($C_1$-$C_6$) alkyl group, especially methyl or ethyl; a lower ($C_2$-$C_6$) alkanoyloxy-lower ($C_1$-$C_6$) alkyl group such as acetoxymethyl, 1-acetoxyethyl and pivaloyloxymethyl; or a lower ($C_1$-$C_6$)alkoxycarbonyloxy-lower ($C_1$-$C_6$) alkyl group such as 1-(ethoxycarbonyloxy) ethyl group.

4. Antibacterial and antifungal activities of benanomicin A, benanomicin B and dexylosylbenanomicin B (as the hydrochloride) are described below.

The minimum inhibitory concentrations (MIC., mcg/ml) of benanomicins A and B against a variety of bacteria and fungi are determined by a standard serial dilution method and shown in Tables 1 and 2 below. The minimum inhibitory concentrations (MIC, mcg/ml) of dexylosylbenanomicin B hydrochloride against a variety of fungi are also determined similarly and shown in Table 2 below. As revealed from Table 2, benanomicins A and B as well as dexylosylbenanomicin B can exhibit substantial antifungal activities against various kinds of fungi.

TABLE 1

| Micro-organism tested (bacteria) | MIC (μg/ml) Benanomicin A | Benanomicin B |
|---|---|---|
| Staphylococcus aureus FDA209P | 100 | >100 |
| Staphylococcus aureus Smith | >100 | >100 |
| Micrococcus luteus FDA16 | 12.5 | 3.12 |
| Bacillus subtilis PCI219 | >100 | >100 |
| Corynebacterium bovis 1810 | 12.5 | 3.12 |
| Mycobacterium smegmatis ATCC607 | >100 | >100 |
| Escherichia coli NIHJ | >100 | >100 |
| Escherichia coli K-12 | >100 | >100 |
| Shigella dysenteriae JS11910 | >50 | >100 |
| Salmonella typhi T-63 | >100 | >100 |
| Proteus vulgaris OX19 | >100 | >100 |
| Pseudomonas aeruginosa A3 | >50 | >100 |
| Klebsiella pneumoniae PCI602 | >100 | >100 |

TABLE 2

| Micro-organism tested (fungi) | MIC (μg/ml) Benanomicin A | Benanomicin B | Dexylosylbenanomicin B |
|---|---|---|---|
| Candida tropicalis F-1 | 25 | >100 | 6.25 |
| Candida pseudotropicalis F-2 | 6.25 | 6.25 | 3.13 |
| Candida albicans 3147 | 25 | 25 | 6.25 |
| Candida Yu-1200 | 12.5 | 12.5 | 6.25 |
| Candida krusei F-5 | 6.25 | 6.25 | 12.5 |
| Saccharomyces cerevisiae F-7 | 6.25 | 12.5 | 6.25 |
| Cryptococcus neoformans F-10 | 3.12 | 1.56 | 3.13 |
| Cochliobolus miyabeanus | >100 | >100 | 50 |
| Pyricularia oryzae | 25 | 50 | 25 |
| Pellicularia sasakii | 25 | 50 | 25 |
| Xanthomonas citri | >100 | >100 | 100 |
| Xanthomonas oryzae | >100 | >100 | 100 |
| Aspergillus niger | 50 | >100 | 25 |
| Trichophyton asteroides 429 | 50 | 25 | 50 |
| Trichophyton mentagrophytes (883) | 50 | 25 | 50 |

5. Toxicity of benanomicins A and B and dexylosylbenanomicin B

When acute toxicity of the new antibiotics of this invention was tested in a mammalian animal upon intravenous administration, it was revealed that the new antibiotics of this invention are of a low acute toxicity. Thus, in an acute toxicity test where benanomicins A and B and dexylosylbenanomicin B were separately administered via intravenous route to Jcl:ICR-strain mice (male, body weight of 19 to 20 g, 5 mice per group), the mice tolerated a dosage of 600 mg/kg of benanomicin A (namely, none of the mice was killed by intravenous administration of benanomicin A at a dose of 600 mg/kg), and the mice also tolerated a dosage of 100 mg/kg of benanomicin B or dexylosylbenanomicin B.

6. Therapeutic effects of benanomicin A on a fungal infection

Curative or therapeutic effects of benanomicin A on an experimental Candida infection in mice were estimated by intravenously inoculating an aqueous suspension (0.2 ml) of a fungus, Candida albicans at a dose of $10^6$ CFU/mouse to Jcl:ICR-strain mice (male, body weight of 19 to 20 g, 5 mice per group) and then subcutaneously or orally administering benanomicin A at different dosages indicated in Table 3 to the mice that have been infected with the Canadida fungus.

The administration of benanomicin A was made three times, namely, directly after the fungal inoculation, 6 hours and 24 hours after the inoculation.

The test results obtained are tabulated in Table 3 below.

TABLE 3

| Dosage of benanomicin A (mg/mouse) | Route of administration | Number of surviving mice | Percent of the number of surviving mice against the tested mice |
|---|---|---|---|
| 0.8 | 3 times*, subcutaneous | 5/5 | 100 |
| 0.4 | 3 times*, subcutaneous | 1/5 | 20 |
| 0.3 | 3 times*, subcutaneous | 2/5 | 40 |
| 0.2 | 3 times*, subcutaneous | 0/5 | 0 |
| Untreated (control) | 3 times*, subcutaneous | 0/5 | 0 |
| 12.0 | 3 times*, oral | 3/5 | 60 |
| 6.0 | 3 times*, oral | 3/5 | 60 |
| 3.0 | 3 times*, oral | 0/5 | 0 |
| 1.5 | 3 times*, oral | 0/5 | 0 |
| Untreated (control) | 3 times*, oral | 0/5 | 0 |

*Administered just after the inoculation, 6 hours later and 24 hours later, respectively.

In a second aspect of this invention, there is provided a process for the production of benanomicin A and/or benanomicin B, which comprises cultivating a benanomicin A and benanomicin B-producing strain of Actinomycetes in a culture medium containing assimilable carbon sources and assimilable nitrogen sources, under aerobic conditions, to produce and accumulate benanomicin A and/or benanomicin B in the resulting culture and then recovering benanomicin A and benanomicin B or one of them from the culture.

In the process according to the second aspect of this invention, the benanomicin A and benanomicin B-producing strain of Actinomycetes which may be used in the process may be cultivated in the culture medium under aerobic conditions at a temperature of 20° to 40° C., preferably of 25° to 37° C., for a time of 3 to 10 days.

A suitable example of the strain capable of producing benanomicin A and benanomicin B which may be used in the process is an Actinomycetes strain MH193-16F4 as detailed in the following.

(a) Microbiological properties of the Actinomycetes strain MH193-16F4

This MH193-16F4 strain is a strain of the family Actinomyces which was isolated in March, 1984 in our laboratory, Zaidan Hojin Biseibutsu Kagaku Kenkyujo from a soil sample as collected in the grounds of this laboratory and to which the laboratory designation of MH193-16F4 has been allotted. Microbiological properties of this strain are as follows.

1. Morphology

The MH193-16F4 strain forms aerial mycelia from branched substrate mycelia when observed under microscope. Fragmentation of substrate mycelia is not observed. Formation of aerial mycelia is observed on ISP-medium 2 and ISP-medium 3 only. Sporulation usually starts at 27° C. from about the 18th day of incubation in ISP-medium 3. Neither whirl formation, nor spirales, nor sporangia are observed on the aerial mycelia, but short sporophore are formed substantially vertically on the aerial mycelia. A chain of usually 3-7 spores, rarely 2 spores is formed at the tip of each sporophore. Spore chains may sometime take a loop-like shape. Individual spores have a cylindrical ($0.8 \times 1.0$-$1.2$ $\mu$m) to spherical ($0.8$-$1.2$ $\mu$m) shape and their surfaces are smooth.

2. Cultural characteristics in various media

The descriptions of colors given in the brackets are made according to the standards of the Color Harmony Manual of Container Corporation of America.

(1) Sucrose-nitrate agar medium (cultured at 27° C.)

Growth was colorless. Aerial mycelia was not formed. No soluble pigment was produced, too. In the same medium but supplemented with vitamin B, the growth was colorless to pinkish gray {5ec, Dusty Peach} in color. Here, aerial mycelia was not formed but soluble pigment was only slightly tinged reddish.

(2) Glucose-asparagine agar medium (cultured at 27° C.)

Growth was colorless. Neither aerial mycelia, nor soluble pigment was produced. In the same medium but supplemented with vitamin B, the growth was colorless to pale pink {4gc, Nude Tan} in color. Here, aerial mycelia was not formed but reddish soluble pigment was formed.

(3) Glycerol-asparagine agar medium (ISP-medium 5, cultured at 27° C.

Growth was colorless, and neither aerial mycelia, nor soluble pigment was produced. In the same medium but supplemented with vitamin B, the growth was a grayish red purple {8lg, Rose Mauve} to dull red purple [8le, Rose Wine} in color, with white aerial mycelia being formed thinnly and with soluble pigment of a dull red purple {8pc, Cranberry} being produced.

(4) Inorganic salts-starch agar medium (ISP-medium 4, cultured at 27° C.)

Growth was colorless, and neither aerial mycelia, nor soluble pigment was formed. In the same medium but supplemented with vitamin B, soluble pigment of a slightly reddish color was produced.

(5) Tyrosine agar medium (ISP-medium 7, cultured at 27° C.)

Growth was colorless to pale yellowish brown {3ic, Lt. Amber} in color. Neither aerial mycelia, nor soluble pigment was produced. In the same medium but supplemented with vitamin B, the growth was colorless to grayish red purple in color. Here, no aerial mycelia was formed but soluble pigment of a slightly reddish color was produced.

(6) Nutrient agar medium (cultured at 27° C.)

Growth was of a pale yellow color {2gc, Bamboo}, with neither aerial mycelia nor soluble pigment being produced. In the same medium but supplemented with vitamin B, the growth showed similar properties.

(7) Yeast extract-malt extract agar medium (ISP-medium 2, cultured at 27° C.)

Growth was a pale yellow {2ec, Biscuit} to dark red {7pi, Dk. Wine-½pe, Dk. Red} to grayish red {7 pg, Wine} in color. From about the 14th day of the incubation, grayish white aerial mycelia was formed on the growth. Although soluble pigment of a dull red color {6½pe, Tomato Red} was produced around the growth at the beginning of the incubation, the soluble pigment then diffused gradually. The color of the growth and the soluble pigment changed to orange colors by reaction with HCl, but showed no color changes upon reaction with NaOH. The growth showed similar properties also in the same medium but supplemented with vitamin B.

(8) Oatmeal agar medium (ISP-medium 3, cultured at 27° C.)

On the growth of a pale pink {4gc, Nude Tan} to grayish red {6le, Cedar} to dark red {7pe, Cherry Wine} to purplish gray {8ig, Mauve Gray} color, aerial mycelia of a grayish white {3cb, Sand} were formed from about the 10th day of the incubation. Soluble pigment was slightly tinged reddish. The color of the growth and the soluble pigment changed to orange colors by reaction with HCl, but showed no color changes upon reaction with NaOH. The growth showed similar properties also in the same medium but supplemented with vitamin B.

(9) Glycerol-nitrate agar medium (cultured at 27° C.)

Growth was colorless, and aerial mycelia was not formed. No soluble pigment was produced. In the same medium but supplemented with vitamin B, the growth showed similar properties.

(10) Starch agar medium (cultured at 27° C.)

Growth was colorless. Neither aerial mycelia, nor soluble pigment was produced. In the same medium but supplemented with vitamin B, the growth was colorless and no aerial mycelia was formed, but soluble pigment was slightly tinged reddish.

(11) Calcium malate agar medium (cultured at 27° C.)

Growth was colorless, and aerial mycelia was not formed. Soluble pigment was slightly tinged reddish. In the same medium but supplemented with vitamin B, the growth was colorless, and neither aerial mycelia, nor soluble pigment was formed.

(12) Cellulose (synthetic test solution containing pieces of filter paper, cultured at 27° C.) No growth was observed.

(13) Gelatin stab culture

Growth was thin both in 15% simple gelatin medium (cultured at 20° C.) and in glucose-peptone-gelatin medium (cultured at 27° C.). The growth was colorless, and neither aerial mycelia, nor soluble pigments was formed.

(14) Skim milk (cultured at 37° C.)

Growth was extremely thin. The growth was colorless, and neither aerial mycelia, nor soluble pigment was formed.

3. Physiological characteristics (1) Growth temperature range

The incubation of the MH193-16F4 strain was tested in a starch-yeast agar medium comprising 1.0% of solubilized starch, 0.2% of yeast extract and 2.0% of agar (pH 7.0), at different incubation temperatures of 20° C., 24° C., 27° C., 30° C., 37° C. and 50° C. As a result, the strain grew at all the tested temperatures except 50° C. However, the optimum growth temperature for this strain appears to be in a range of from about 27° C. to 37° C.

(2) Liquefaction of gelatin (in 15% simple gelatin medium, cultured at 20° C., and in glucose-peptone-gelatin medium, cultured at 27° C.)

No liquefaction of gelatin was observed in the simple gelatin medium and in the glucose-peptone-gelatin medium during the incubation of the strain for 3 months.

(3) Hydrolysis of starch (in inorganic salts-starch agar medium and in starch agar medium, both, cultured at 27° C.)

Hydrolysis of starch did not start when the strain was incubated in the inorganic salts-starch agar medium and also in the starch agar medium.

(4) Coagulation and peptonization of skim milk (in skim milk, cultured at 37° C.)

Growth was thin, and neither coagulation nor peptonization of skim milk was observed during the incubation of the strain for 3 months.

(5) Formation of melanoid pigments (in tryptone-yeast extract broth, ISP-medium 1; peptone-yeast extract iron agar, ISP-medium 6; tyrosine agar, ISP-medium 7; all cultured at 27° C.)

Formation of melanoids were negative in all the media.

(6) Utilization of carbon sources (in Pridham-Gottlieb agar medium, ISP-medium 9; cultured at 27° C.)

When the strain grows, glucose, L-arabinose, D-xylose, D-fractose, sucrose, rhamnose, raffinose and D-mannitol are utilizable but inositol is not.

(7) Liquefaction of calcium malate (in calcium malate agar, cultured at 27° C.)

Negative.

(8) Reduction of nitrate (in Bacto-nitrate broth, ISP-medium 8, cultured at 27° C.)

Positive.

(9) Degradation of cellulose (in a synthetic test solution containing pieces of filter paper, cultured at 27° C.)

The strain does not grow.

Summarizing the above-mentioned microbiological properties, the MH193-16F4 strain is characterized in that spore chains of 3-7 spores (rarely 2 spores) are formed substantially vertically on main stems of aerial mycelia, and that neither whirl formation, nor spirals nor sporangia are observed. In addition, no fragmentation of the substrate mycelia is observed. Spore surfaces are smooth. Aerial mycelia of a grayish white color are formed thinly on the growth of grayish red to dark red color both in ISP-medium 2 and in ISP-medium 3. When the MH193-16F4 strain is successively incubated in a slant medium comprising 0.2% yeast extract, 1.0% of solubilized starch and 2.0% of agar (pH 7.0), aerial mycelia of a pink color may sometime be formed. Further, soluble pigment of a dull red color is produced in ISP-medium 2. In various other culture media, the growth was colorless, and aerial mycelia was not formed, but soluble pigment is substantially not produced. Its growth is however promoted by addition of vitamin B to the culture media. There are some culture media in which the strain grows with a red color. The colors of the growth and the soluble pigment both change from a red color to an orange color by reaction with HCl, but do not change by reaction with NaOH. Formation of melanoids, proteolytic activity and starch-hydrolyzability are all negative, while reduction of nitrate are positive. The growth may be promoted in culture media supplemented with vitamin B in some instances, so that the strain seems to demand vitamins for its growth.

Incidentally, the MH193-16F4 strain contains mesodiaminopimelic acid as the cell wall components and glucose, ribose and madurose as the saccharide components in the whole cells, and shows that the main constituents of the cell wall are of the Type-IIIB proposed by Lechevalier et al. in the "International Journal of Systematic Bacteriology", 20, 435 (1970). On the other hand, its phospholipids are of the P IV type (comprising phosphatidylethanolamine and unknown glycosamine-containing phospholipids but not comprising phosphatidyl glycerol). The composition of menaquinones comprises MK-9($H_8$) as a principal component and also MK-9($H_6$), MK-9($H_4$), MK9($H_2$), MK-9($H_{10}$), and the content of GC in the DNA amounted to 71.5%. An analysis of the mycelia by gas chromatography reveals that iso-branched fatty acids (i-16:0), antiiso-branched fatty acids (a-17:0) and 10-methyl fatty acid (10Me-17:0) are present, giving the characteristic features of the strain.

Among known strains of Actinomycetes, those which form the chain of spores and show the cell wall components of the Type-IIIB are belonging to the three genera, Actinomadura, Microbispora and Microtetraspora. Characteristic features of the MH193-16F4 strain and the above-described three genera are shown in Table 4. The asterisk (*) attached to a menaquinone indicates that such menaguinone is present as a principal component.

As is apparent from Table 4, it does not appear that there is any genus to which the MH193-16F4 strain belongs evidently in every aspect. The above-mentioned three genera have been transitional with delicacy. It is hence interesting how these genera will be defined in the next edition of Bergey's Manual of Determinative Bacteriology. However, many species are listed under the genus Actinomadura and the properties of such species vary widely. Significant similarity is found in the morphology, the fatty acid composition of the mycelia and the composition of menaquinones between the MH193-16F4 strain and *Actinomadura spadix* among such species of Actinomadura {see the cited literatures 1), 3) and 5)}. We, the present inventors, therefore plans to conduct at first a comparative experiment between the 7. MH193-16F4 strain and *Actinomadura spadix*. It seems however very probable that the MH193-16F4 strain belongs to the genera Actinomadura and may make a novel species.

Incidentally, the MH193-16F4 strain has been deposited in a Japanese depository "Fermentation Research Institute", Agency of Industrial Science and Technology, Ministry of International Trade and Industry, Japanese Government, under the deposit number FERM P-9529 since Aug. 21, 1987. The MH193-16F4 strain has now been deposited in the "Fermentation Research Institute" in terms of the Budapest Treaty under the deposit number "FERM BP-2051".

(b) Cultivation of the MH193-16F4 strain

The production of benanomicins A and B is carried out by inoculating a benanomicin A and benanomicin B-producing strain of Actinomycetes to a culture medium containing such nutrient sources which can be utilized by ordinary microorganisms, and then incubating said benanomicin-producing strain under aerobic

TABLE 4

|  | MH193-16F4 | Microbispora | Microtetraspora | Actinomadura |
|---|---|---|---|---|
| Cell wall type[1] | IIIB | IIIB | III B | III B |
| Phospholipid[1] | P IV | P IV | P IV, P I | P I, P IV |
| Menaquinones[1,2,3] | *MK-9($H_8$), MK-9($H_2$), MK-9($H_4$), MK-9($H_6$), MK-9($H_{10}$) | *MK-9($H_6$), MK-9($H_4$), MK-9($H_8$), or MK-9($H_0$), MK-9($H_2$), MK-9($H_4$), or *MK-9($H_4$), MK-9($H_2$), MK-9($H_6$) | *MK-9($H_6$), MK-9($H_2$), MK-9($H_4$), or MK-9($H_0$), MK-9($H_2$), MK-9($H_4$), or *MK-9($H_4$), MK-9($H_6$), | *MK-9($H_6$), MK-9($H_4$), MK-9($H_8$) or *MK-9($H_4$), MK-9($H_2$), MK-9($H_0$) or *MK-9($H_8$), MK-9($H_6$) or *MK-9($H_4$), MK-9($H_6$) |
| Fatty acids[3] | Composite type (i-16:0, a-17:0, 10Me-17:0) | Composite type (i-16:0, a-17:0, 10Me-17:0, n-15:0) | — | Linear type (i-16:0, 10ME-17:0, 18:0, n-17:0, 18:1) Composite type (i-16:0, a-17:0, 10Me-17:0, 16:1) |
| GC content (%) | 71.5 | 73.7 (67)[2] | (66-67)[2] | 70-78 (66-68)[2] |
| State of formation of spores | Almost vertical. Loop-like in some instances. | Vertical | Not always vertical | Not always vertical, loop-like, spiral |
| Pseudosporangia[1] | None | None | None | None or positive |
| Spore-surface[1,4,5] | Smooth | Smooth or spiny | Smooth | Smooth or warty |
| Number of spores | 3-7 (rarely 2) | 2 | 4 (1-6) | 5-15 |
| Color of aerial mycelia[1] | Grayish white, pink | Pink, white | White, grayish white, gray, yellowish green | White, pink, gray, blue, green, yellow |
| Vitamin-demand[1] | + | + | + | + |
| Growth temperature[1] | Mesophilic | Mesophilic or thermophilic | Mesophilic | Mesophilic |

With regard to the literatures cited in the above table:-
[1] A Japanese literature "Hosenkin no Dotei Jikkenho (Experiments for the identification of Actinomycetes) ", compiled by Nihon Hosenkin Kenkyukai (1985).
[2] J. Poschner, et al., "DNA-DNA Reassociation and Chemotaxonomic Studies on Actinomadura, Microbiapora, Microtetraspora, Micropolyspora and Nocardiopsis." in the "Systematic and Applied Microbiology", 6, 264-270, (1985).
[3] A Fisher, et al., "Molecular-genetic and Chemotaxonomic Studies on Actinomadura and Nocardiopsis." in the "Journal of General Microbiology", 129, 3433-3446, (1983).
[4] Thiemann, et al., "A New Genus of the Actinomycetales: Microtetraspora gen. nov." in the "Journal of General Microbiology", 50, 295-303, (1968).
[5] Nonomura, et al., a Japanese article "Dojochu ni okeru Hosenkin no Bunpu (Distribution of Actinomycetes in Soil) (11th Report) Several New Species of Actinomadura Lechevalier et al." in a Japanese literature "Hakko Kogaku Kaishi", 49, 904-912, (1971).

conditions. Benanomicin A and B are produced and accumulated primarily in the culture broth. The target antibiotics are recovered from the resulting culture, especially from the culture broth or its filtrate.

The nutrient sources available in the culture medium to be used may be any of the conventional nutrient sources which have been useful as nutrient sources for the cultivation of known strains of Actinomycetes. For example, the assimilable nitrogen sources may include soybean meal, peptone, meat extract, corn steep liquor, cotton seed meal, peanut meal, dry yeast, yeast extract, NZ-amine, casein, sodium nitrate, ammonium sulfate and ammonium nitrate which are commercially available. The assimilable carbon sources may include glycerin, sucrose, starch, glucose, galactose, maltose, dextrin, lactose, molasses, soybean oil, fat and amino acids, which are commercially available. The culture medium may also contain inorganic salts such as sodium chloride, phosphates, calcium carbonate, magnesium sulfate, cobalt chloride and manganese chloride. In addition, trace amounts of metal salts, and one or more of animal, vegetable or mineral oils as defoaming agents can also be added. They may be any materials so long as they can be utilized by the benanomicins-producing strain and are useful for the production of benanomicins A and B. Known nutrient materials for cultivation of known strains of Actinomycetes are all usable.

Liquid cultivation method is preferred for the production of benanomicins A and B in a large scale. The cultivation temperature may be chosen within the range of the temperatures at which the benanomycins-producing microorganism can grow and can produce benanomicins A and B. The cultivation temperature may generally be at 20°–40° C., preferably at 25°–37° C. The cultivation can be conducted by choosing the above-mentioned conditions of the cultivation properly in accordance with the natures of the microorganism which can produce benanomicins A and B.

(c) Recovery and Purification of benanomicins A and B

For recovery of benanomicins A and B from the resulting culture of the microorganism capable of producing benanomicins A and B, benanomycins A and B can be extracted from the culture or the culture broth filtrate and then purified by using conventional methods for recovery and purification, for example, solvent extraction, ion-exchange resin method, adsorptive or partition column chromatography, gel filtration, dialysis, precipitation and the like, either singly or in combination. For example, benanomicins A and B can be recovered from the incubated mycelia cake by extracting with acetone-water or methanol-water. On the other hand, benanomicins A and B which have been produced and accumulated in the culture broth or the filtrate can be adsorbed on an adsorbent such as a microporous non-ionic resinous adsorbent, for example, "DIAION HP-20" (trade name; synthetic resinous adsorbent produced by Mitsubishi Kasei Corporation, Japan). In addition, when the culture broth or the broth filtrate is extracted with an organic solvent immiscible with water, e.g., butanol, ethyl acetate or the like, benanomicin A and B substances are extracted in the organic solvent phase.

According to a particular embodiment of the process of the second aspect of this invention, the MH193-16F4 strain (identified as FERM BP-2051) is cultivated in a culture medium under aerobic conditions at a temperature of 25° to 37° C., preferably for 3 to 10 days, to produce and accumulate benanomicin A and benanomicin B in the resulting culture broth, the culture broth is filtered, and the resultant culture broth filtrate is passed through a column of an adsorbent to effect the adsorption of benanomicin A and benanomicin B by the adsorbent, and benanomicin A and benanomicin B are separately recovered by chromatographically eluting the column of the adsorbent containing benanomicins A and B adsorbed therein.

For mutual isolation and further purification of benanomicins A and B, chromatographic method with use of an adsorbent such as silica gel ("WAKOGEL C-300", trade name, product of Wako Pure Chemical Industries, Ltd.), and alumina or a gel-filtration agent "Sephadex LH-20" (trade name; product of Pharmacia AB), or the like may be made suitably.

Benanomicins A and B as produced in the culture as described above can be isolated in their free form, namely, as benanomicins A and B themselves as such.

When a solution containing benanomicins A and/or B or its concentrated solution is treated with a basic compound, for example, an inorganic base, including an alkali metal compound such as sodium hydroxide or potassium hydroxide, an alkaline earth metal compound such as calcium hydroxide or magnesium hydroxide, and an ammonium salt; as well as an organic base such as ethanolamine, triethylamine or dicyclohexylamine during the operation of one of steps for the recovery, for example, during the step of the extraction, isolation or purification, it happens that benanomicin A and/or B are or is converted into the corresponding salts which may then be separated or isolated in the form of such salts or salt.

Further, the salt of benanomicin A or B produced as described above can then be converted into the free form, namely benanomicin A or B as such when treated by a method known per se in the art for the conversion of a salt into an acid. In addition, benanomicins A and/or B obtained in the free form may again be converted into the corresponding salts or salt by reaction with the above-mentioned base in a usual manner. Equally to benanomicins A and B, their salts such as those exemplified above should therefore be embraced in the scope of the present invention.

In the third aspect of this invention, there is further provided a process for the production of dexylosylbenanomicin B, namely the compound of the formula (Ic) defined hereinbefore, which comprises converting chemically benanomicin B into dexylosylbenanomicin B.

Here, by the term "converting chemically benanomicin B" is meant either an acidic hydrolysis of benanomicin B, or an alcoholysis of benanomicin B followed by treatment of the resulting dexylosylbenanomicin B ester with a basic compound to form dexylosylbenanomicin B. When benanomicin B is hydrolyzed with an acid, the xylosyl group of benanomicin B molecule is simply cleaved, affording the desired dexylosylbenanomicin B. When benanomicin B undergoes an alcoholysis with an alcohol, for example, a lower ($C_1$–$C_6$) alkanol such as methanol and ethanol, the xylosyl group is cleaved and concurrently the carboxyl group of benanomicin B molecule is esterified with said alcohol, giving an ester of dexylosylbenanomicin B, which may subsequently be treated with a basic compound for alkaline hydrolysis so that dexylosylbenanomicin B in the free form is produced.

According to a particular embodiment of the process of the third aspect of this invention, there is provided a process for the production of dexylosylbenanomicin B, which comprises cleaving the xylosyl group from benanomicin B either by acidic hydrolysis, or by alcoholysis followed with treatment with a basic compound, to form the dexylosylbenanomicin B. In this embodiment, the acidic hydrolysis of benanomicin B may be effected by reacting an inorganic or organic acid with benanomicin B in aqueous solution at a temperature of 60° to 110° C., preferably for 5 to 15 hours. When the acidic hydrolysis of benanomicin B is effected by reacting with a routinely usable inorganic or organic acid such as hydrochloric acid, sulfuric acid, acetic acid, trifluoroacetic acid, p-toluenesulfonic acid or benzenesulfonic acid, dexylosylbenanomicin B is produced in the reaction solution.

Further, the alcoholysis of benanomicin B may generally be effected by heating a solution of benanomicin B in a lower ($C_1$-$C_6$) alkanol, preferably methanol and ethanol, in the presence of an inorganic acid such as hydrochloric acid, sulfuric acid and nitric acid at a temperature of 60° to 120 ° C., preferably for 5 to 15 hours, to produce such an ester (the carboxylate) of the dexylosylbenanomicin B as formed with said alkanol. This dexylosylbenanomicin B ester so formed may then be hydrolytically treated by reacting with a basic compound, for example, an alkali metal hydroxide or carbonate, preferably sodium or potassium hydroxide or carbonate in aqueous solution at room temperature or at an elevated temperature so that the dexylosylbenanomicin B is produced. Thus, when benanomicin B is subjected to alcoholysis, for example, methanolysis, and then treated with a base such as sodium hydroxide or potassium hydroxide, dexylosylbenanomicin B is produced in the reaction solution.

In order to recover dexylosylbenanomicin B as produced from the reaction solution, this product can be extracted therefrom and then purified by using conventional methods for recovery and purification, for example, solvent extraction, ion-exchange resin method, adsorptive or partition column chromatography, gel filtration, dialysis, precipitation and the like, either singly or in combination. For example, dexylosylbenanomicin B in the aqueous reaction solution can be adsorbed on a adsorbent resin "DIAION HP-20" (trade name; synthetic resinous adsorbent produced by Mitsubishi Kasei Corporation). For further purification of dexylosylbenanomicin B, chromatographic method with use of an adsorbent such as silica gel ("WAKOGEL C-300", trade name, product of Wako Pure Chemical Industries, Ltd.; or the like) alumina and a gel-filtration agent "Sephadex LH-20" (trade name; product of Pharmacia AB), or the like may again be made suitably.

Dexylosylbenanomicin B as formed in the reaction solution as described above can be isolated in the free form, namely, as dexylosylbenanomicin itself. A solution containing dexylosylbenanomicin B or its concentrated solution may be treated with a routinely usable acid, for example, an inorganic acid such as hydrochloric acid, sulfuric acid, phosphoric acid and nitric acid, or an organic acid such as acetic acid and an alkylsulfonic acid, or an inorganic base, for example an alkali metal compound such as sodium hydroxide or potassium hydroxide; an alkaline earth metal compound such as calcium hydroxide or magnesium hydroxide; and an ammonium salt, or an organic base such as ethanolamine, triethylamine or dicyclohexylamine during operation of one step for the recovery and purification. Then, dexylosylbenanomicin B is converted into the corresponding salt and may further be isolated in the form of the salt. Further, the dexylosylbenanomicin B salts so produced can then be converted into the free form, namely, dexyloxylbenanomicin B itself when treated by a method known per se in the art. In addition, dexylosylbenanomicin B obtained in the free form may again be converted into a salt by reaction with the above-mentioned acid or base in a usual manner. Further, when reacting dexylosylbenanomicin B with an alcohol, for example, a lower alkanol such as methanol and ethanol, the corresponding ester at its carboxyl group may be formed.

In a further aspect of this invention, there is provided an antifungal composition for therapeutic treatment of a fungal infection in an animal, including human, which comprises an antifungally effective amount of a compound of the general formula (I) as defined hereinbefore, namely one of benanomicins A and B, dexylosylbenanomicin B and their salts or esters, as active ingredient, in association with a pharmaceutically acceptable solid or liquid carrier.

In another aspect of this invention, there is provided a method for treating a fungal infection, especially a Candida⁻ infection, in an animal, including human, which comprises administering an antifungally effective amount of benanomicin A, benanomicin B, dexylosylbenanomicin B or a salt or ester thereof to the animal that has been infected with a fungus, especially a fungus of the genus Candida.

This invention also includes use of benanomicin A, benanomicin B, dexylosylbenanomicin B or a salt or ester thereof in a pharmaceutical composition.

The pharmaceutical composition containing the compound of the general formula (I) or a salt or ester thereof may be formulated in a known manner into a conventional formulation for administration, for example, powder, granules, tablets, pills and capsules for oral administration, as well as intravenously, intramuscularly or subcutaneously injectable solution, and suppositories, using a pharmaceutically acceptable solid or liquid carrier which is suitable for the formulation. Suitable solid carrier may include sugars such as maltose and sucrose, amino acid, cellulose derivatives such as hydroxy-propylcellulose, and cyclodextrins, for instance. Suitable liquid carrier may include water, alcohols such as ethanol, soybean oil and other various oils, as well as physiological saline solution, for instance. The formulation may contain the compound of the formula (I) usually in a proportion of 0.1 to 90% by weight, depending on the form of the formulation. An injectable solution may generally contain 0.1 to 10% by weight of the new compound of this invention. Dosage of the new compound of this invention may be decided according to various factors such as age, body weight, conditions of patients, kind of fungal infection and purposes of the therapeutic treatment, and merely for the purpose of a guideline, the new compound of this invention may be given at a dose of 1 to 300 mg/kg per day for non-oral administration and at a dose of 5 to 500 mg/kg per day for oral administration.

This invention is now illustrated with reference to the following Examples, to which this invention is not limited in any way. Thus, the detailed properties of benanomicins A and B and also dexylosylbenanomicin B have been made evident by this invention and hence it is feasible for the skilled in the art to contemplate and perform the processes of producing benanomicins A and B or dexylosylbenanomicin B in different ways with taking into account the above-described properties of these compounds. Accordingly, this invention embraces not only any modification of the procedures of the following Examples, but also all such processes wherein benanomicines A and B or dexylosylbenanomicin B are produced, concentrated, extracted and/or purified in a manner known per se with utilizing the properties of benanomicins A and B or dexylosylbenanomicin B.

EXAMPLE 1

A loopful quantity of the MH193-16F4 strain (identified as FERM BP-2051), which had been incubated in a slant agar medium, was inoculated into 80 ml of a liquid culture medium comprising 1.0% starch and 3.0% soybean meal (pH 7.0 before the sterilization) which was placed in a Sakaguchi's flask of 500 ml-capacity. The inoculated culture medium was incubated at 28° C. for 3 days under shaking (135 rpm.) to provide a first seed culture. The first seed culture obtained was inoculated in 3 ml-portions into 80 ml-portions of the liquid culture medium having the same composition as above, which were separately placed in many Sakaguchi's flasks. The inoculated culture media were incubated for 3 days under the same incubation conditions as above, to give the second seed culture. The resultant second seed culture (2 litres) was then inoculated to a culture medium (50 litres) of the same composition as above which had been sterilized at 120° C. for 15 minutes and was placed in a tank-fermentor of 100 l-capacity. The so inoculated culture medium was then incubated at 28° C. for 2 days under aeration at a rate of 50 l of air per minute and under agitation at 200 rpm. to effect the submerged cultivation of the MH193-16F4 strain under aerobic conditions and obtain a third seed culture. The resultant third seed culture (12 litres) was inoculated into a productive culture medium (300 litres) comprising 2.0% of glycerin, 1.5% of soybean meal (available commercially under a tradename "Esusan Meat", a product of Ajinomoto Co. Ltd., Japan), 0.0025% of $K_2HPO_4$, 0.1125% of $KH_2PO_4$, 0.0005% of $CoCl_2.6-H_2O$, 0,03% of a silicone oil "KM72" (a defoaming agent, a trade name of a product of Shinetsu Chemicals Co. Ltd., Japan) and 0.01% of a surfectant "Adekanol" (a trade name, product of Asahi Denka Kogyo Co. Ltd., Japan) which had preliminarily been sterilized at 125° C. for 30 minutes and was placed in a tank-fermentor of 570 l-capacity. The cultivation was conducted at 28° C. for 7 days under agitation at 300 rpm. and under aeration at a rate of 150 l of air per minute for the first 24 hours of the cultivation and then at a rate of 300 l of air per minute after the 24th hour of the cultivation. After the completed cultivation, the culture broth obtained was mixed with diatomaceous earth as a filtration-aid and then filtered to give 250 l of the culture broth filtrate (pH 6.0).

EXAMPLE 2

The culture broth filtrate (250 l) obtained in the above Example 1 was passed through a column of 15 l of a microporous non-ionic adsorbent resin "DIAION HP-20" to effect the adsorption of the active substances by the adsorbent. After the adsorbent column was washed with 100 l of water and with 45 l of 50% aqueous methanol, the adsorbent column was eluted with 45 l of 70% aqueous methanol and then with 90 l of dry methanol, so that the first fraction (53 l), second fraction (38 l) and third fraction (27 l) of the eluate were obtained separately. The first fraction containing the active substance was concentrated to 3 l under reduced pressure, followed by adjustment to pH 3.5 with dilute hydrochloric acid to deposit a precipitate of a red color. The precipitate was collected by filtration and then dried under reduced pressure, whereby 152 g of a crude brown powder mainly comprising benanomicin A was obtained.

150 Grams of the crude powder was dissolved in 600 ml of dimethylformamide. After saturation of the resultant solution with water vapor at room temperature for 3 days in a desiccator, a crystalline precipitate was deposited. The precipitate was collected by filtration and then dried under reduced pressure, thereby obtaining 29 g of benanomicin A-dimethylformamide solvate. The second fraction of the eluate was processed in the same way as the first fraction, thereby obtaining 14 g of benanomicin A-dimethylformamide solvate.

One gram of the benanomicin A-dimethylformamide solvate as obtained from said first fraction was dissolved in dimethylsulfoxide (5 ml). The resultant solution was added dropwise under stirring into 300 ml of methanol, followed by stirring for 10 minutes to deposit a precipitate of a reddish brown color. The precipitate was filtered out and then dried under reduced pressure, to afford 935 mg of a purified benanomicin A as reddish brown powder.

EXAMPLE 3

The third fraction of the eluate as obtained in the Example 2 was concentrated to 1.5 l under reduced pressure, followed by its adjustment to pH 3.5 with dilute hydrochloric acid, to obtain a precipitate of red color. The precipitate was collected by filtration and then dried under reduced pressure, whereby 98 g of a crude brown powder containing benanomicin B was obtained. One gram of this crude powder was dissolved in 10 ml of dimethylformamide at 40° C. and the resulting solution was passed through a column of 1 l of a gel-filtration agent "Sephadex LH-20" which had been soaked with dimethylformamide, and then the "Sephadex" column was developed with dimethylformamide. The eluate was collected in 6 ml-fractions. Fraction Nos. 64–72 containing the active substance were collected, combined and then concentrated to dryness under reduced pressure, whereby 657 mg of a crude brown powder comprising benanomicin B-dimethylformamide solvate was obtained. Three hundred milligrams of this crude powder were dissolved in 100 ml of methanol, and after addition of 1 ml of 1 N hydrochloric acid, the solution was concentrated to dryness under reduced pressure. The resultant crude powder of a brown color was dissolved in 3 ml of dimethylsulfoxide. The resulting solution was added dropwise to 200 ml of chloroform under stirring, followed by stirring for 20 minutes to deposit a reddish brown precipitate. The precipitate was collected by filtration and then dried under reduced pressure, to yield 258 mg of benanomicin B hydrochloride in a purified form.

EXAMPLE 4

This Example illustrates the production of dexylosylbenanomicin B by acidic hydrolysis of benanomicin B.

Benanomicin B hydrochloride (130 mg) was dissolved in 10 ml of water, followed by addition of 10 ml of concentrated hydrochloric acid. The resultant mixture was sealed in a glass tube. After effecting the hydrolysis reaction at 110° C. for 12 hours, the resultant precipitate was collected by filtration. The precipitate was extracted three times with 10 ml of dioxane, so that 47.5 mg of benanomicinone (aglycone of benanomicin B) was obtained. The residue which remained after the extraction was purified by a preparative silica gel thin layer chromatography (on silica gel "Art. 5744", trade name, product of Merck & Co., Inc.; as developed with a mixed solvent of butanol-acetic acid-pyridine=6:1:4), whereby Fraction 1 containing dexylosylbenanomicin B and Fraction 2 containing benanomicinone were obtained separately. Fraction 1 was adsorbed on 20 ml of an adsorbent "DIAION HP-20". After washing the adsorbent with water (60 ml), the adsorbent was eluted four times with 40 ml of methanol. The eluate was concentrated to dryness, the residue obtained was dissolved in 3 ml of water, and the resultant solution was adjusted to pH 2 with 0.1 N hydrochloric acid. When concentrating the solution to dryness, 17.8 mg of a purified dexylosylbenanomicin B hydrochloride was obtained. Similarly, Fraction 2 was purified chromatogrophically using the adsorbent "DIAION HP-20", when 9.5 mg of benanomicinone was recovered.

EXAMPLE 5

This Example illustrates the production of dexylosylbenanomicin B by methanolysis of benanomicin B followed by the treatment with a basic compound, sodium hydroxide.

Forty ml of a solution of 217 mg of benanomicin B hydrochloride in 1 N HCl - methanol were sealed in a glass tube and heated at 90° C. for 12 hours for the alcoholysis. The reaction solution was thereafter concentrated to dryness. The residue was dissolved in 30 ml of water and adsorbed on 100 ml of an adsorbent "DIAION HP-20". The adsorbent was then washed with water (300 ml), followed by extraction four times with 200 ml of methanol. The extract solution was concentrated to dryness to obtain 125 mg of the methyl ester of dexylosylbenanomicin B as formed. The methyl ester obtained was dissolved in 20 ml of water, and after addition of 5 ml of 1 N NaOH, the alkaline hydrolysis of the ester was effected at room temperature for 10 minutes. After addition of 7 ml of 1 N hydrochloric acid to the reaction solution, the resultant mixture was concentrated to dryness. The residue was dissolved in 20 ml of water and the solution was adsorbed on a column of 100 ml of an adsorbent "DIAION HP-20". After washing the adsorbent column with 300 ml of water, the adsorbent was eluted with 200 ml of methanol. The solution obtained was concentrated to dryness, and then passed through a column of 650 ml of a gel-filtration agent "Sephadex LH-20". The "Sephadex" column was developed with methanol. Active fractions of the eluate were collected, combined and concentrated to dryness. The resultant residue was dissolved in 10 ml of water, and the solution was adjusted to pH 2 with 1 N hydrochloric acid. When concentrating the solution to dryness, 109.5 mg of a purified dexylosylbenanomicin B hydrochloride was obtained as a reddish brown powder.

We claim:

1. A compound which is Benanomicin A of the formula (Ia)

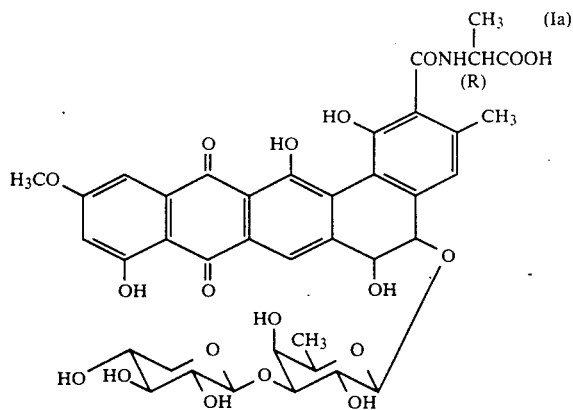

or a salt or an ester of benanomicin A.

2. A compound as claimed in claim 1, which is in the form of a salt (carboxylate) thereof with an alkali metal or an alkaline earth metal or in the form of an ester (carboxylate) thereof with a lower alkyl group, a lower alkanoyloxy-lower alkyl group such as acetoxymethyl, 1-acetoxyethyl and pivaloyloxymethyl, or a lower alkoxycarbonyloxy-lower alkyl group such as 1-(ethoxycarbonyloxy)ethyl group.

3. An antifungal composition which comprises an antifungally effective amount of benanomicin A of formula (Ia) as defined in claim 1, or a salt or an ester thereof, as active ingredient in association with a pharmaceutically acceptable solid or liquid carrier.

* * * * *